United States Patent
Anderson et al.

(10) Patent No.: US 10,532,504 B2
(45) Date of Patent: Jan. 14, 2020

(54) APPARATUS AND METHOD USABLE WITH AN INJECTION MOLDER FOR PRODUCING ARTICLES

(71) Applicant: DENTSPLY International Inc., York, PA (US)

(72) Inventors: Michael Anderson, Bradenton, FL (US); David Richard Maroney, Cedar, MN (US)

(73) Assignee: DENTSPLY SIRONA INC., York, PA (US)

(*) Notice: Subject to any disclaimer, the term of this patent is extended or adjusted under 35 U.S.C. 154(b) by 1377 days.

(21) Appl. No.: 14/153,269

(22) Filed: Jan. 13, 2014

(65) Prior Publication Data
US 2014/0197574 A1    Jul. 17, 2014

Related U.S. Application Data

(60) Provisional application No. 61/751,591, filed on Jan. 11, 2013.

(51) Int. Cl.
*B29C 45/16* (2006.01)
*B29C 45/33* (2006.01)
*B29C 45/00* (2006.01)

(52) U.S. Cl.
CPC .......... *B29C 45/33* (2013.01); *B29C 45/0055* (2013.01)

(58) Field of Classification Search
CPC ................ B25C 2045/067; B29C 45/0408
See application file for complete search history.

(56) References Cited

U.S. PATENT DOCUMENTS

| | | | |
|---|---|---|---|
| 5,087,504 A * | 2/1992 | Kanai | B29C 45/1657 285/336 |
| 5,622,494 A | 4/1997 | Andreiko et al. | |
| 5,954,501 A | 9/1999 | Masumoto et al. | |

FOREIGN PATENT DOCUMENTS

| | | |
|---|---|---|
| DE | 19920941 A1 | 11/2000 |
| EP | 0495219 A2 | 7/1992 |
| EP | 1033193 A1 | 9/2000 |
| KR | 101033230 B1 | 5/2011 |

* cited by examiner

*Primary Examiner* — Galen H Hauth
(74) *Attorney, Agent, or Firm* — McNees Wallace & Nurick LLC

(57) ABSTRACT

An apparatus usable with an injection molder for producing articles includes a first mold support including a first mold, and a second mold support including a second mold and a first die. The first mold support is movable relative to the second mold support between a first position and a second position. In the first position, the first mold and the second mold being brought together to form an injection molded article include a body having at least one protrusion extending outwardly from the body and facing the second mold. In the second position, the first mold and the first die being brought together to subsequently form the article, the first die selectively subsequently forming an altered cross sectional region in at least a portion of the protrusion, forming an undercut in the altered cross sectional region or between the altered cross sectional region of the subsequently formed protrusion and the body.

19 Claims, 21 Drawing Sheets

APPARATUS AND METHOD USABLE WITH AN INJECTION MOLDER FOR PRODUCING ARTICLES

CROSS-REFERENCE TO RELATED APPLICATIONS

This application claims the benefit of and priority to U.S. Provisional Application No. 61/751,591 filed Jan. 11, 2013, which is hereby incorporated by reference in its entirety.

FIELD

The present invention relates to orthodontic articles and more particularly to orthodontic brackets.

BACKGROUND

In the past, various difficulties have been encountered in connection with the orthodontic necessity to apply corrective appliances to human teeth pursuant to which certain teeth are displaced to a position of better alignment, and/or occlusion.

One primary need in orthodontic corrections is the maintenance of relatively high tensile forces on the teeth, particularly in cases where substantial displacements are required.

In response, brackets have been utilized, i.e., wire guiding and wire anchoring means which do not encircle individual teeth. However, there continue to be challenges associated with such brackets, which are difficult to apply since the cold curing cement used to affix the brackets to the teeth does not adhere well to the brackets. In practice, this inadequate adhesion has resulted in the application of reduced forces, reducing the effectiveness of orthodontic corrective treatment.

There is a need in the art for an apparatus and method for reliably increasing adherence of orthodontic brackets to teeth surfaces for use in orthodontic corrective treatment.

SUMMARY

In an exemplary embodiment, an apparatus usable with an injection molder for producing articles includes a first mold support including a first mold and a second mold support including a second mold and a first die. The first mold support is movable relative to the second mold support between a first position and a second position. In the first position, the first mold and the second mold being brought together to form an injection molded article include a body having at least one protrusion extending outwardly from the body and facing the second mold. In the second position, the first mold and the first die being brought together to subsequently form the article, the first die selectively subsequently forming an altered cross sectional region in at least a portion of the protrusion, forming an undercut in the altered cross sectional region or between the altered cross sectional region of the subsequently formed protrusion and the body.

In another exemplary embodiment, an apparatus usable with an injection molder for producing articles includes a first mold support including at least two first molds, and a second mold support including at least two second molds and at least two first dies. The first mold support is rotatably movable relative to the second mold support between a first position and a second position. In the first position, each of the corresponding first molds and second molds being brought together to form an injection molded article include a body having at least one protrusion extending outwardly from the body and facing the second mold. In the second position, each of the corresponding first molds and first dies being brought together to subsequently form the article, each first die selectively subsequently forming an altered cross sectional region in at least a portion of the subsequently formed protrusion, forming an undercut in the altered cross sectional region or between the altered cross sectional region of the subsequently formed protrusion and the body.

In yet another exemplary embodiment, a method of producing injection molded articles includes providing a first mold support including a first mold, a second mold support including a second mold and a first die. The method further includes bringing the first mold support and the second mold support together, the first mold and the second mold being brought together to form an injection molded article therebetween, the article having at least one protrusion facing the second mold. The method further includes moving the first mold support away from the second mold support and moving the first mold support relative to the second mold support. The method further includes bringing the first mold support and the second mold support together, the first mold and the first die being brought together to subsequently form the article, the first die selectively subsequently forming an altered cross sectional region in at least a portion of the subsequently formed protrusion, forming an undercut in the altered cross sectional region or between the altered cross sectional region of the subsequently formed protrusion and the body.

Other features and advantages of the present invention will be apparent from the following more detailed description of the preferred embodiment, taken in conjunction with the accompanying drawings which illustrate, by way of example, the principles of the invention.

DETAILED DESCRIPTION OF EXEMPLARY EMBODIMENTS

Exemplary embodiments are directed to apparatus and method usable with an injection molder for producing articles, such as orthodontic brackets comprising bodies having at least one protrusion extending outwardly from the corresponding bodies. An altered cross sectional region is formed in at least a portion of at least one protrusion, forming an undercut in the altered cross sectional region or between the altered cross sectional region of the at least one protrusion and the body, as will be discussed in further detail below. The undercut provides enhanced adherence of the subsequently formed orthodontic brackets to teeth surfaces for use in orthodontic corrective treatment.

For purposes herein, an undercut is intended to correspond to an altered cross sectional region formed in a protrusion that is positioned in the altered cross sectional region or between the altered cross sectional region of the protrusion and the body of an article. Stated another way, in or coincident with the altered cross sectional region or between the body of an article and the altered cross sectional region of a protrusion extending outwardly from the body, the protrusion of a subsequently formed article includes a subsequently formed portion having at least a localized altered cross sectional area relative to the cross sectional area of the protrusion. When the localized altered cross sectional region is greater than the cross sectional area of the protrusion, the undercut or region of reduced cross sectional area is positioned between the localized altered cross sectional region and the body. However, when the localized altered cross sectional region is less than the cross sectional area of the protrusion, the undercut corresponds to the localized altered cross sectional region itself, such as at least a partial recess formed in the side surface of the protrusion.

Neither arrangement can be produced by conventional molds of an injection molder, as a die constructed to produce protrusions having undercuts cannot be nondestructively separated from corresponding injection molded articles (i.e., the corresponding rigid injection molded articles would be destroyed while separating the molds producing the article).

Figure 1:
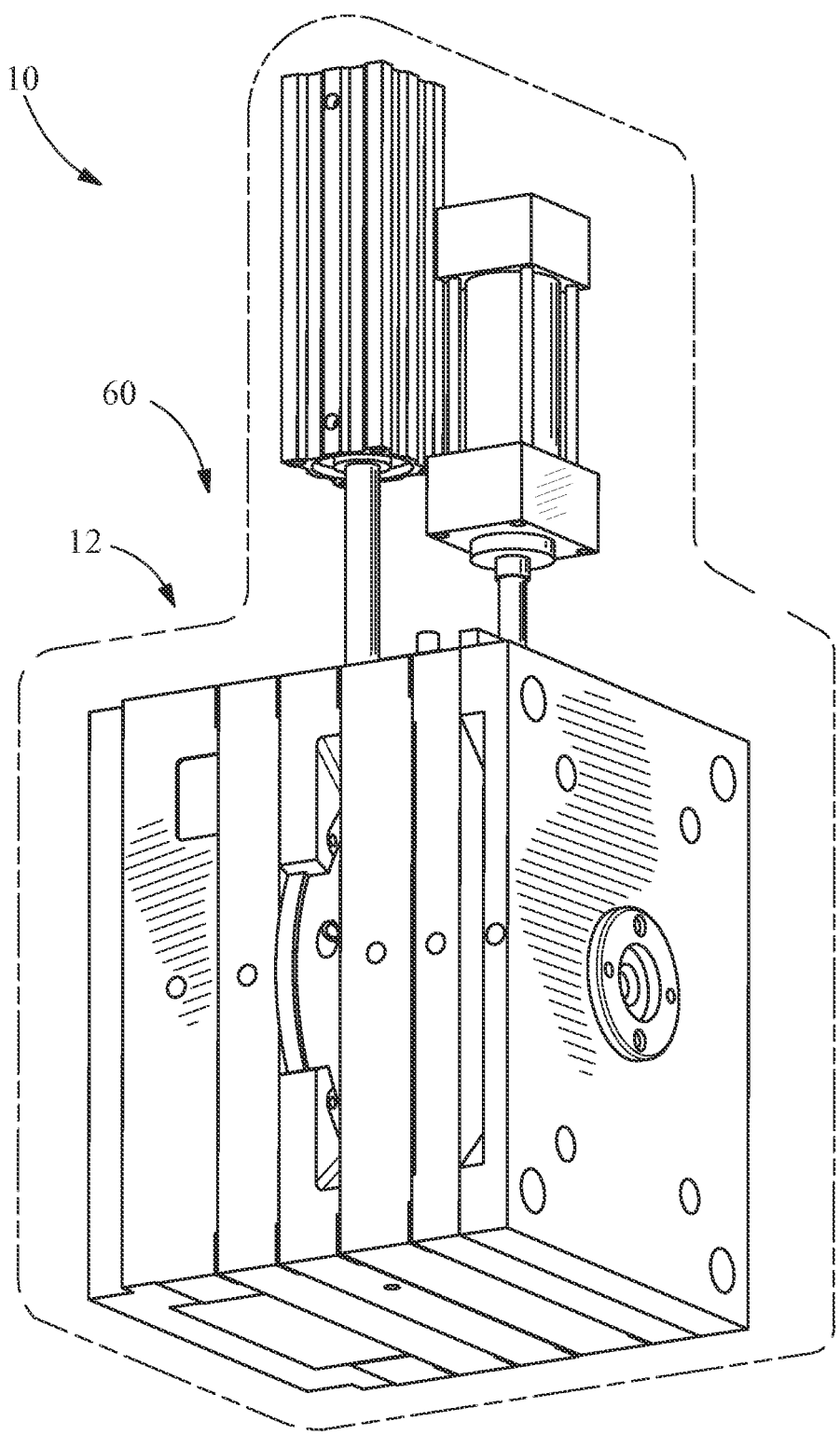
FIG. 1 is a lower perspective view of an exemplary injection molder and apparatus according to the disclosure.

As shown in FIG. 1, an injection molder 10 includes an apparatus 12 further including mold supports 18, 20 (FIG. 2) in a closed position 60. Injection molder 10, which is well known in the art, is not further discussed.

Figure 2:
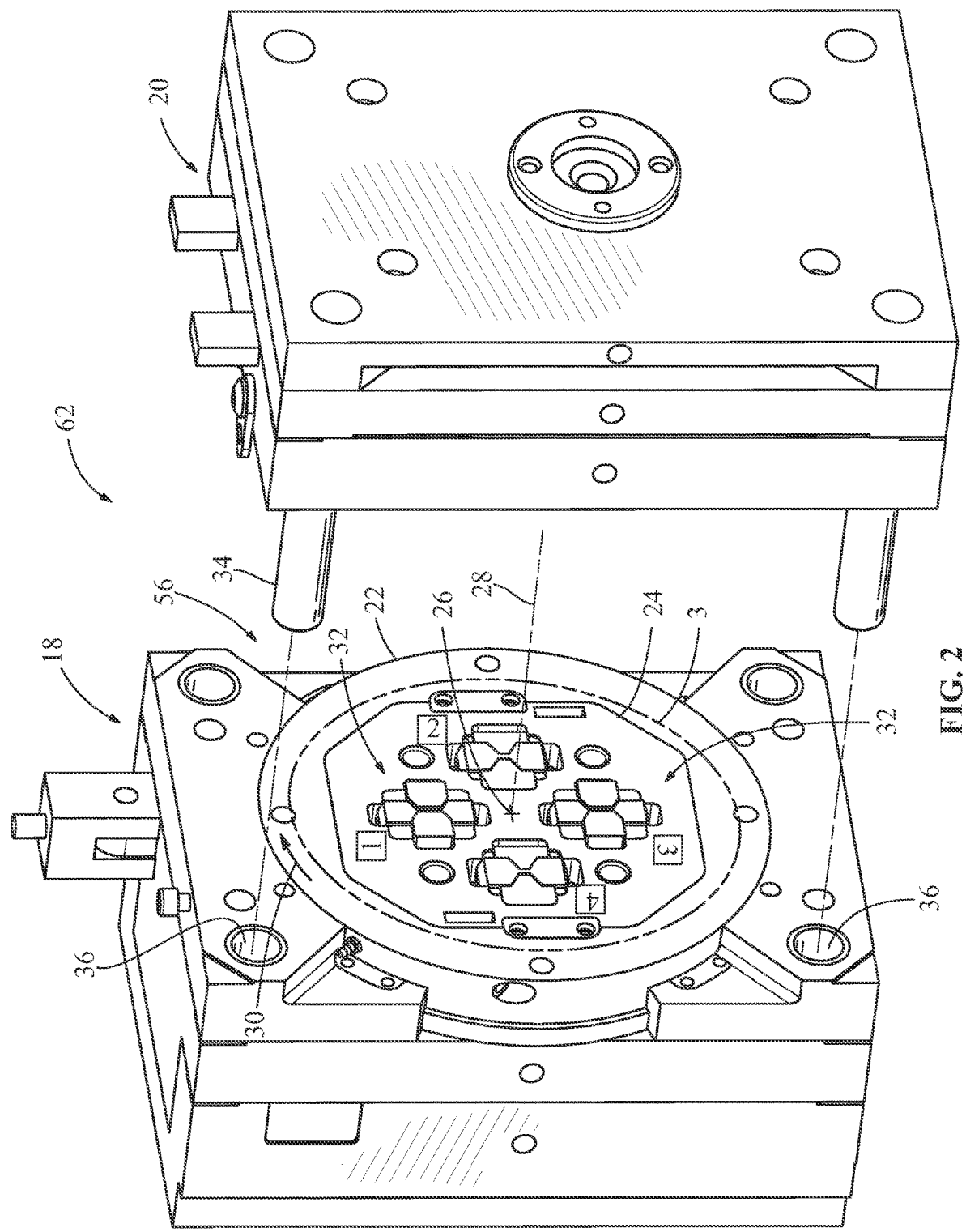
FIG. 2 is an upper perspective view of an exemplary apparatus in an open position and an exemplary mold in a first position according to the disclosure.
Figure 3:
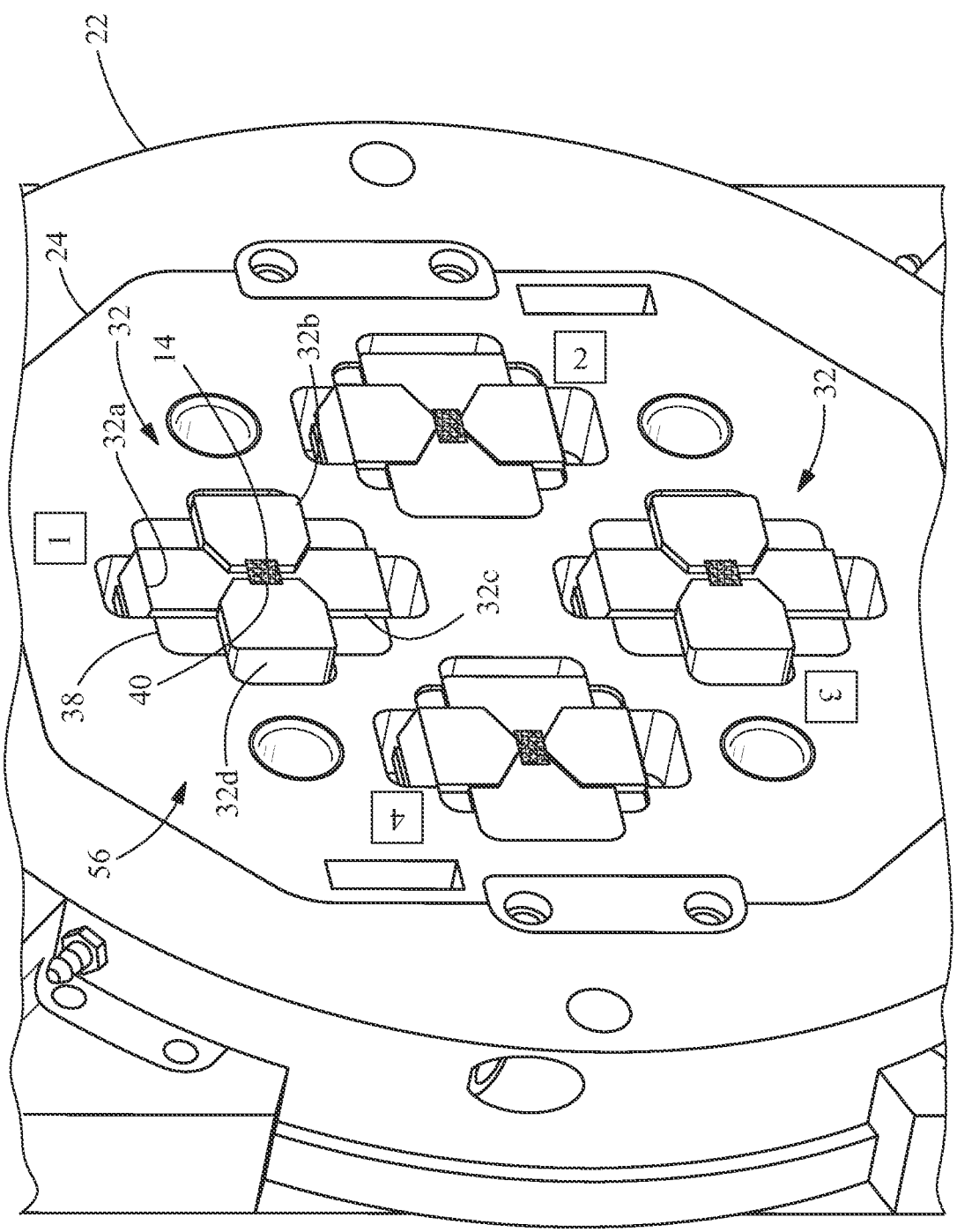
FIG. 3 is an enlarged, partial view of an exemplary mold taken from region 3 of FIG. 2 according to the disclosure.

As collectively shown in FIGS. 2 and 3, mold supports 18, 20 are shown in an open position 62, versus closed position 60 (FIG. 1), movable along a line of engagement 11 between mold support alignment features 34, 36, such as respective mating openings and pins formed in mold supports 18, 20. Mold support 18 includes mold support portions 22, 24, in which mold support portion 22 can be selectively urged into rotational movement 30, relative to mold support 20, about an axis 28 extending through a center 26 of mold support portion 22. As further shown in FIG. 2, mold support portion 24 structurally supports a plurality of molds 32 (four molds 32 are shown in FIG. 2) arranged in a first position 56. In other embodiments, as few as one mold, or more than four molds may be supported by mold support portion 24. As further shown in FIG. 2, for purposes of describing the operation of the apparatus of the present disclosure, mold 32 associated with a numeral 1 enclosed in a box and located at a 12 o'clock position in FIG. 2 is primarily discussed herein and is associated with first position 56 (although FIG. 2 shows additional molds 32 associated with respective numerals 2, 3 and 4 located at respective 3 o'clock, 6 o'clock and 9 o'clock positions). As shown in further detail in FIG. 3, mold 32 includes mold segments 32a, 32b, 32c, 32d that are slidably structurally supported by a guide 38. In one embodiment, mold 32 may be of unitary or one-piece construction (i.e., having no mold segments), although in other embodiments, mold 32 may include less than four or more than four mold segments, as required. As further shown in FIG. 3, mold segments 32a, 32b, 32c, 32d collectively define a cavity 40 for forming an article 14 by injection molding. In addition, mold support 20 includes a mold 44 (FIGS. 4-6) for use in forming article 14, as further discussed below.

Figure 4:
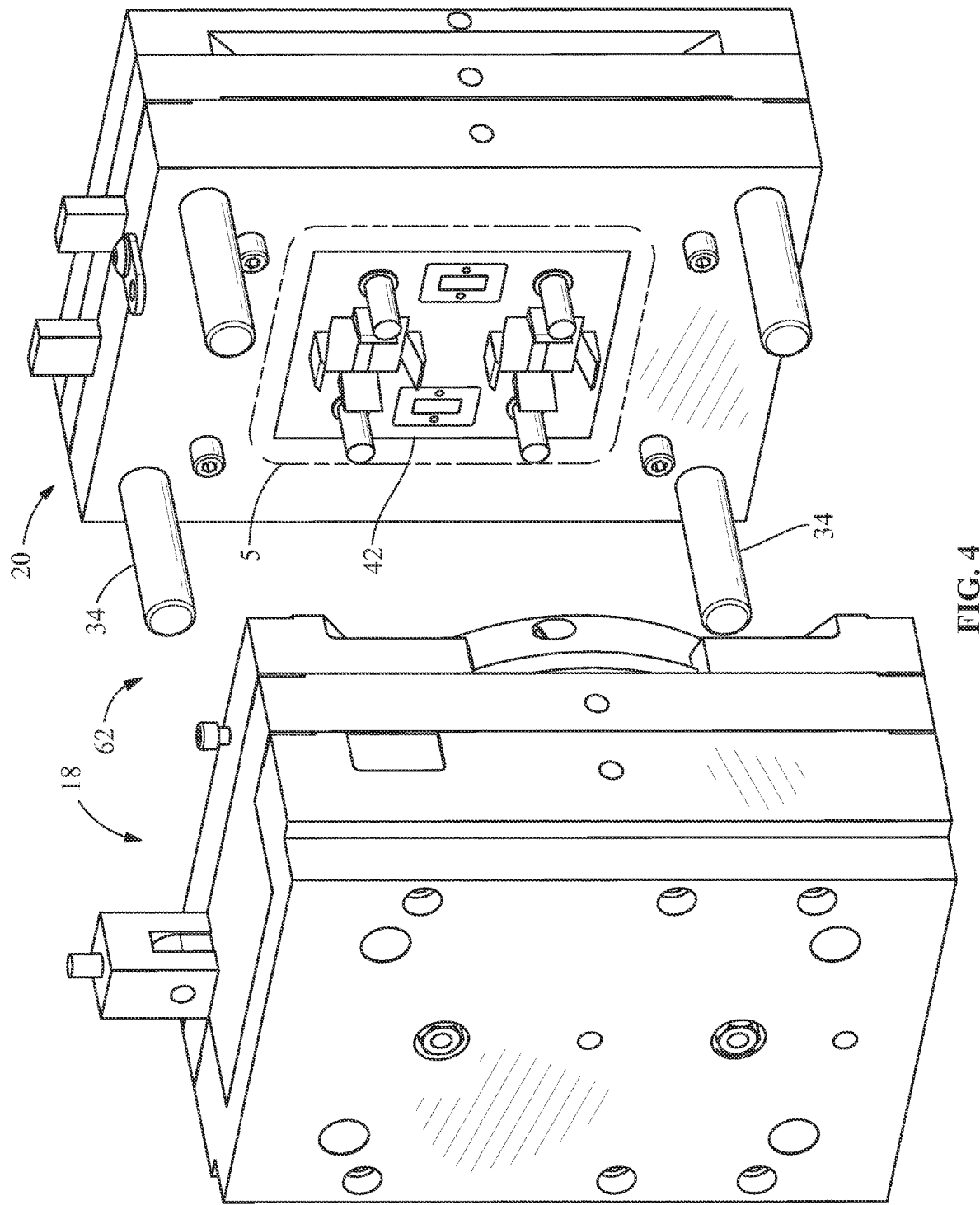
FIG. 4 is a reverse upper perspective view, relative to FIG. 2, of the exemplary apparatus of FIG. 2 according to the disclosure.
Figure 5:
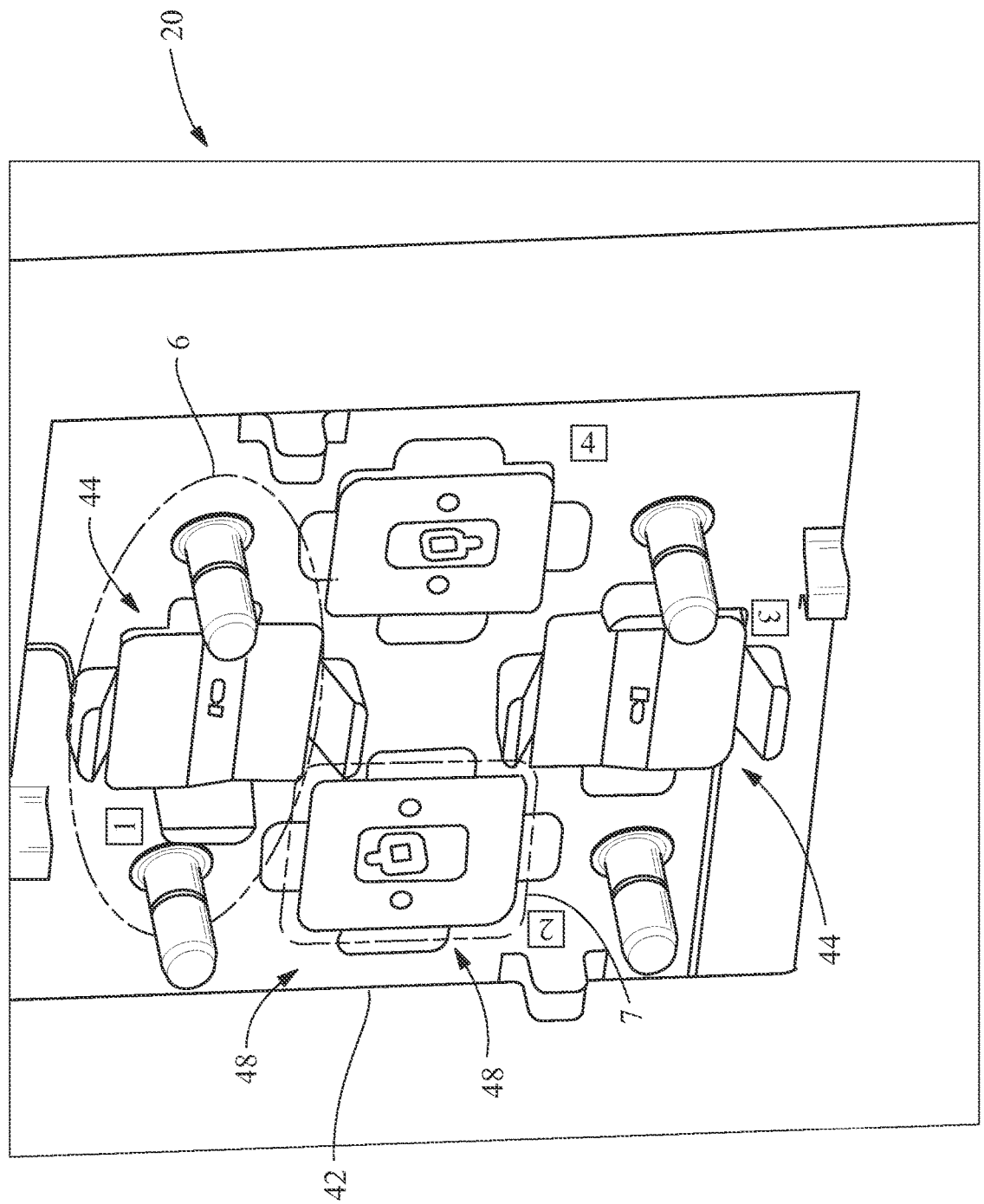
FIG. 5 is an enlarged, partial view of an exemplary mold taken from region 5 of FIG. 4 according to the disclosure.
Figure 6:
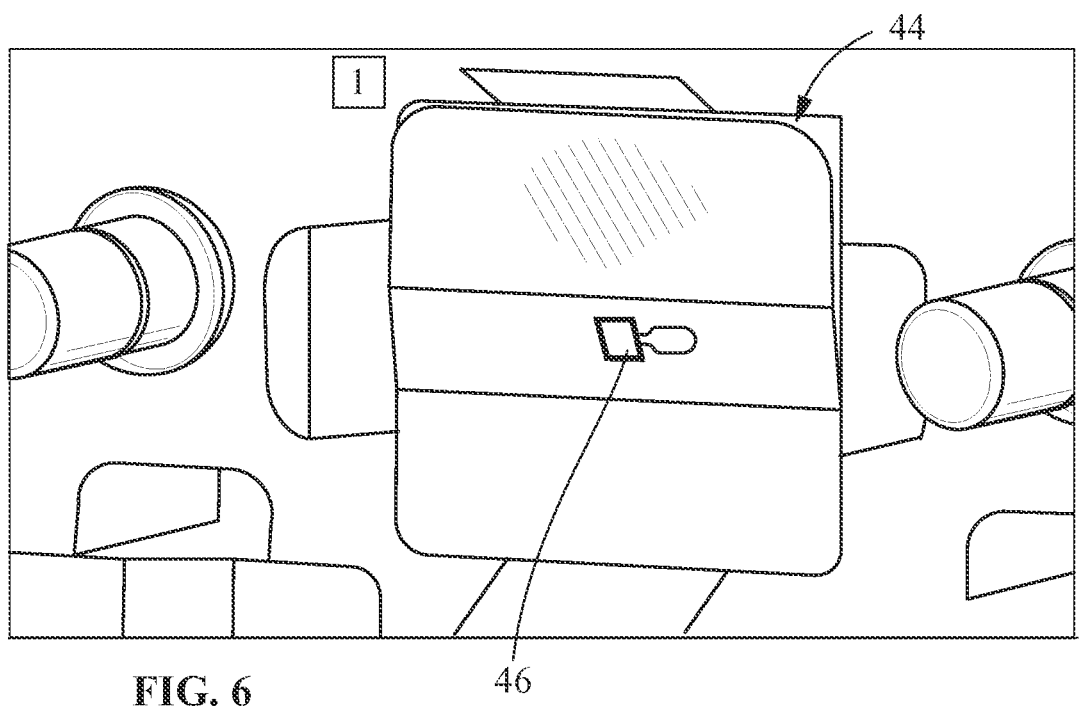
FIG. 6 is a further enlarged, partial view of an exemplary mold taken from region 6 of FIG. 5 according to the disclosure.
Figure 7:
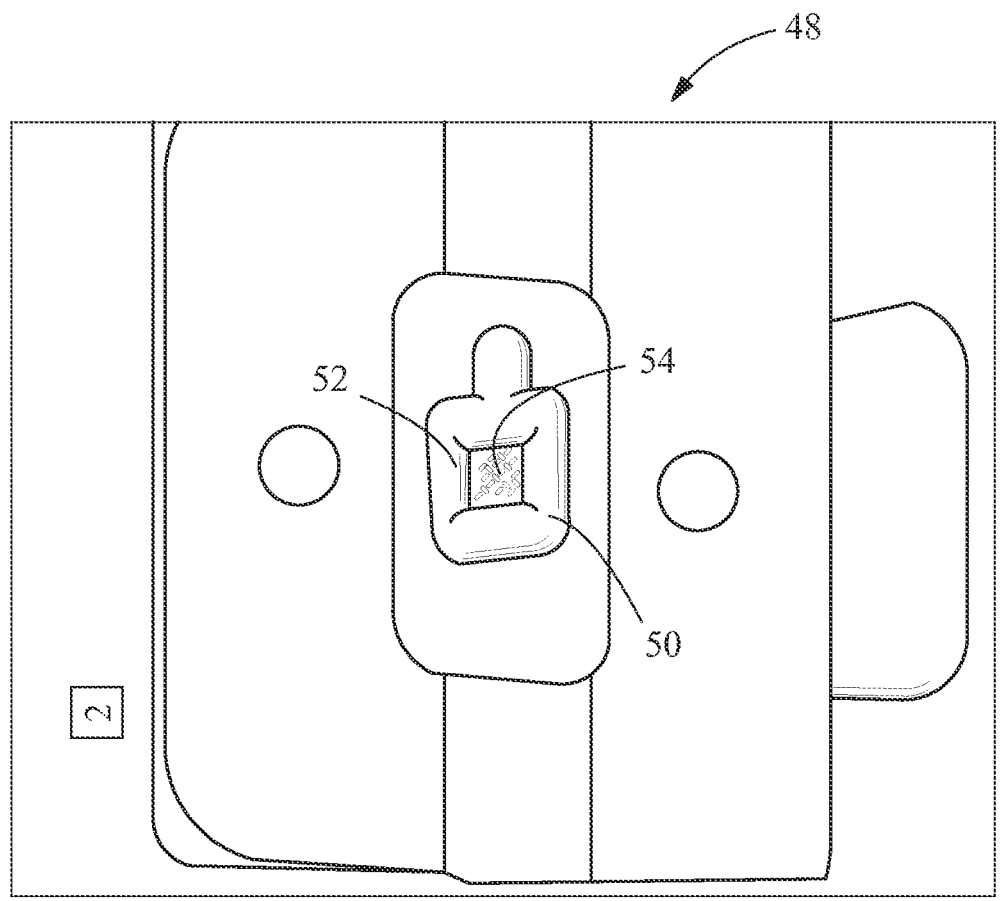
FIG. 7 is an enlarged, partial view of an exemplary die taken from region 7 of FIG. 5 according to the disclosure.
Figure 8:
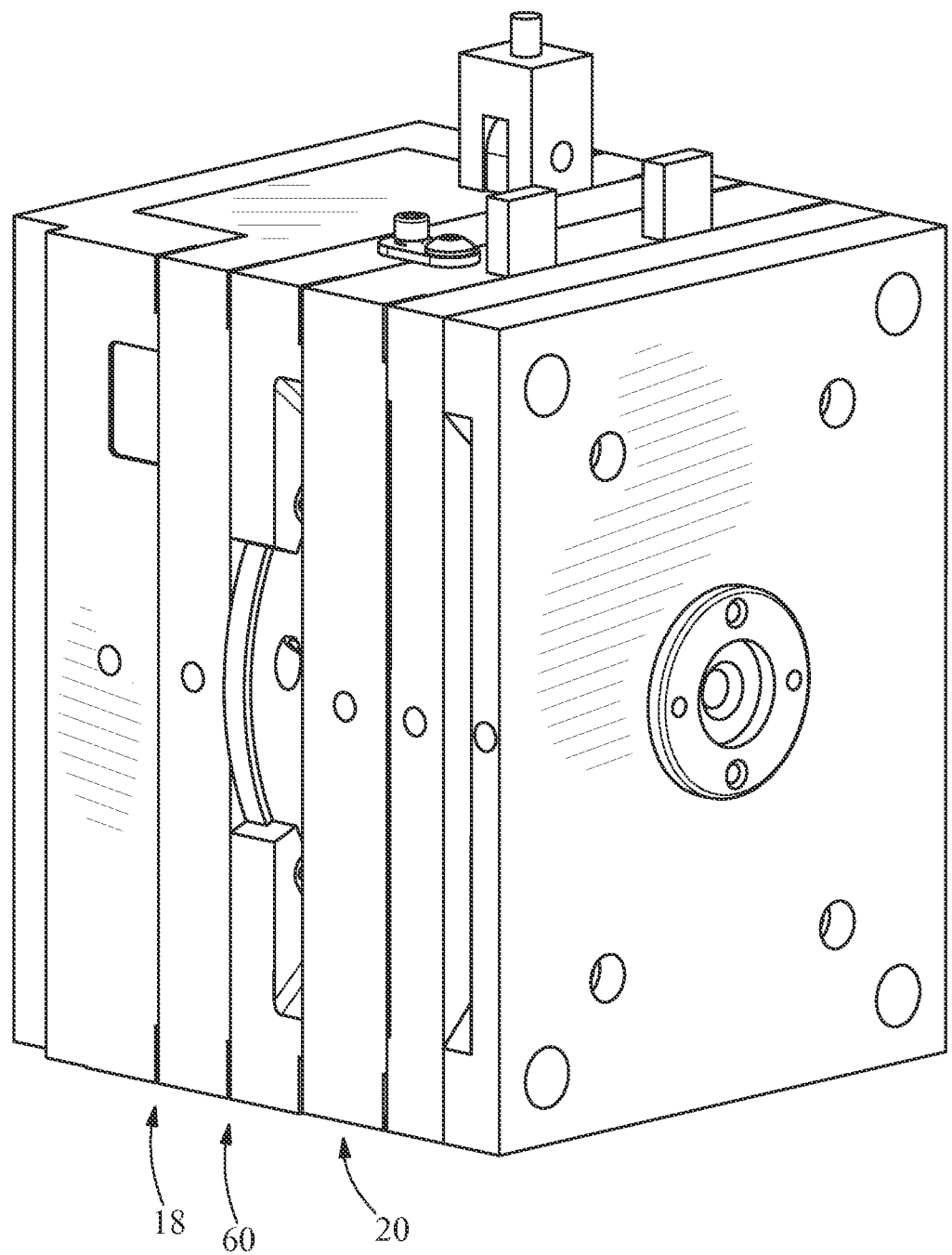
FIG. 8 is an upper perspective view of an exemplary apparatus in a closed position according to the disclosure.
Figure 13:
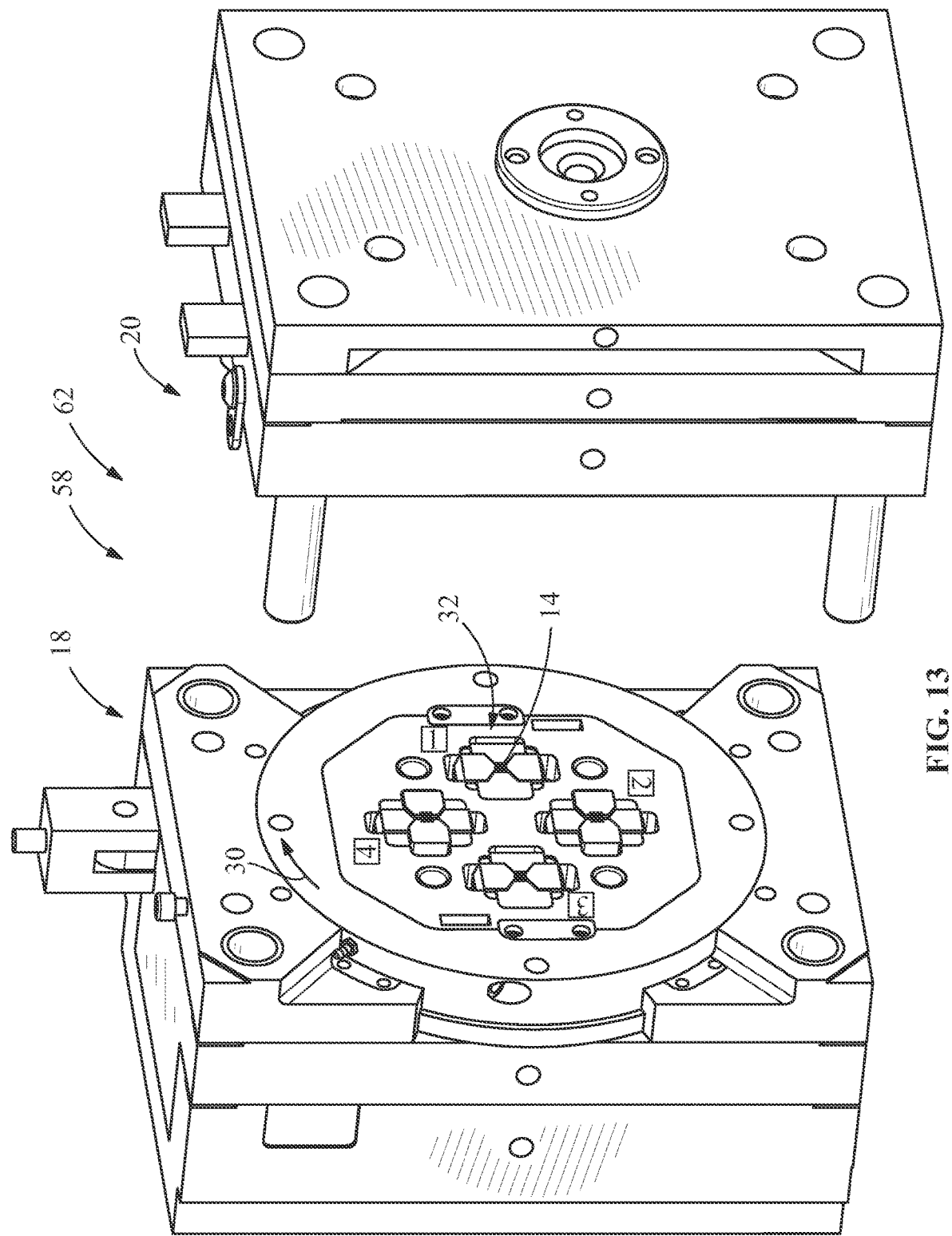
FIG. 13 is an upper perspective view of the exemplary apparatus in an open position and the exemplary mold of FIG. 12 in the second position according to the disclosure.
Figure 14:
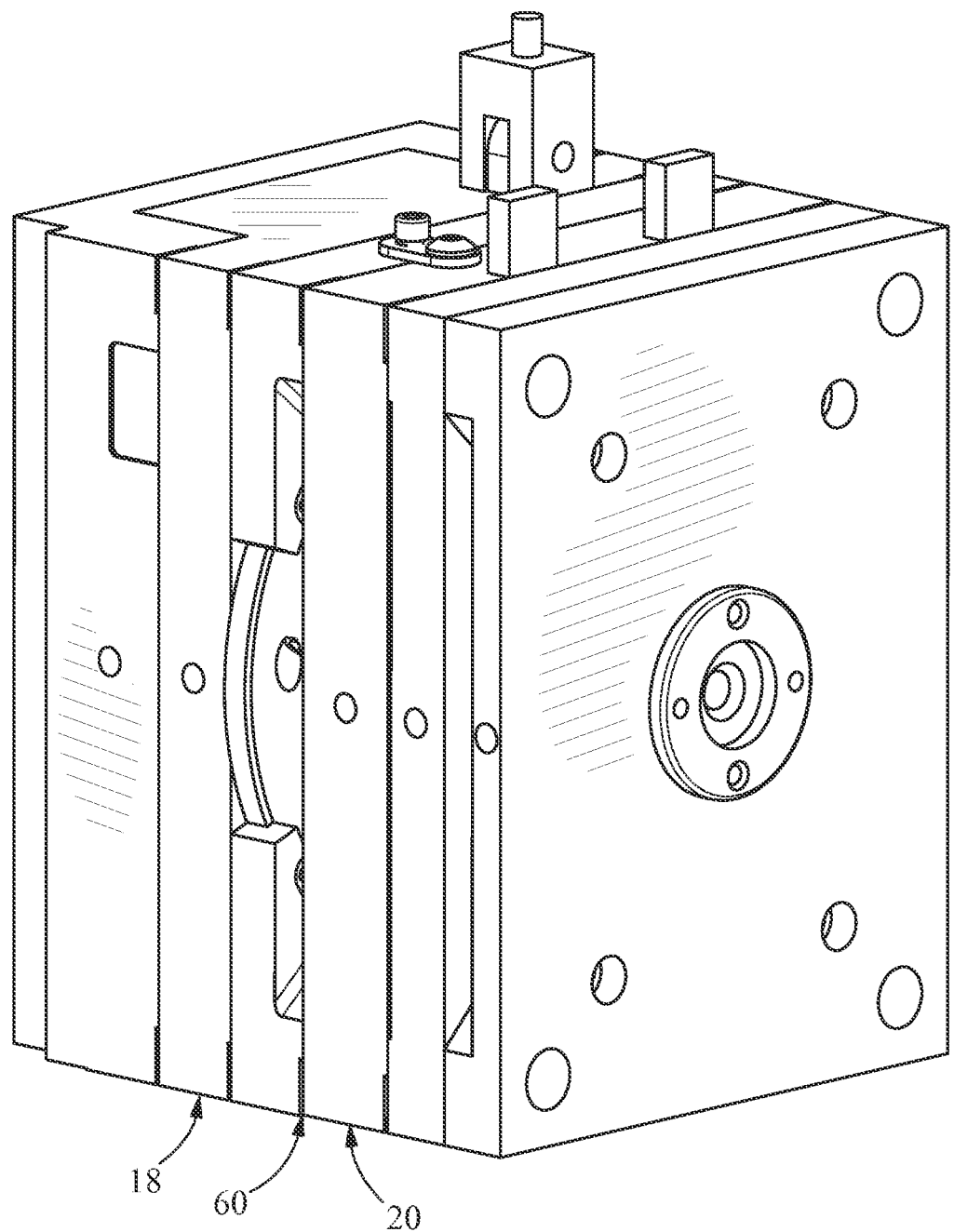
FIG. 14 is an upper perspective view of the exemplary apparatus of FIG. 13 in a closed position according to the disclosure.

As further shown in FIGS. 4-7, mold support 20 includes a mold/die support portion 42 structurally supporting a pair of molds 44 associated with respective boxed numerals 1 and 3 located at respective 12 o'clock and 6 o'clock positions (FIG. 4). As further shown in FIGS. 5 and 6, mold 44 associated with boxed numeral 1 in the 12 o'clock position (FIG. 4) corresponds to mold 32 in the 12 o'clock position (FIG. 3) which are brought together (e.g., as shown in FIG. 8) to form article 14 therebetween in first position 56 of mold 32 of mold support 18, with mold 32 defining cavity 40 (FIG. 3) and mold 44 including a mold surface 46 (FIG. 6). As further shown in FIGS. 4, 5 and 7, mold/die support portion 42 of mold support 20 also structurally supports a pair of dies 48 associated with respective boxed numerals 2 and 4 located at respective 9 o'clock and 3 o'clock positions (FIG. 4). Die 48 includes a peripheral recess 50 (FIG. 7), providing an outwardly extending member 52 that terminates at a die surface 54. As will be discussed in more detail below, die 48 (FIGS. 4, 5, 7) associated with boxed numeral 2 located at the 9 o'clock position is brought together (e.g., as shown in FIG. 14) with the corresponding mold 32 (FIG. 13) to subsequently form and thereby transforming article 14 to subsequently formed article 16.

In one embodiment, mold support 20 structurally supports one mold 44 and one die 48, while in another embodiment, mold support 20 structurally supports more than two molds 44 and more than two dies 48.

Figure 9:
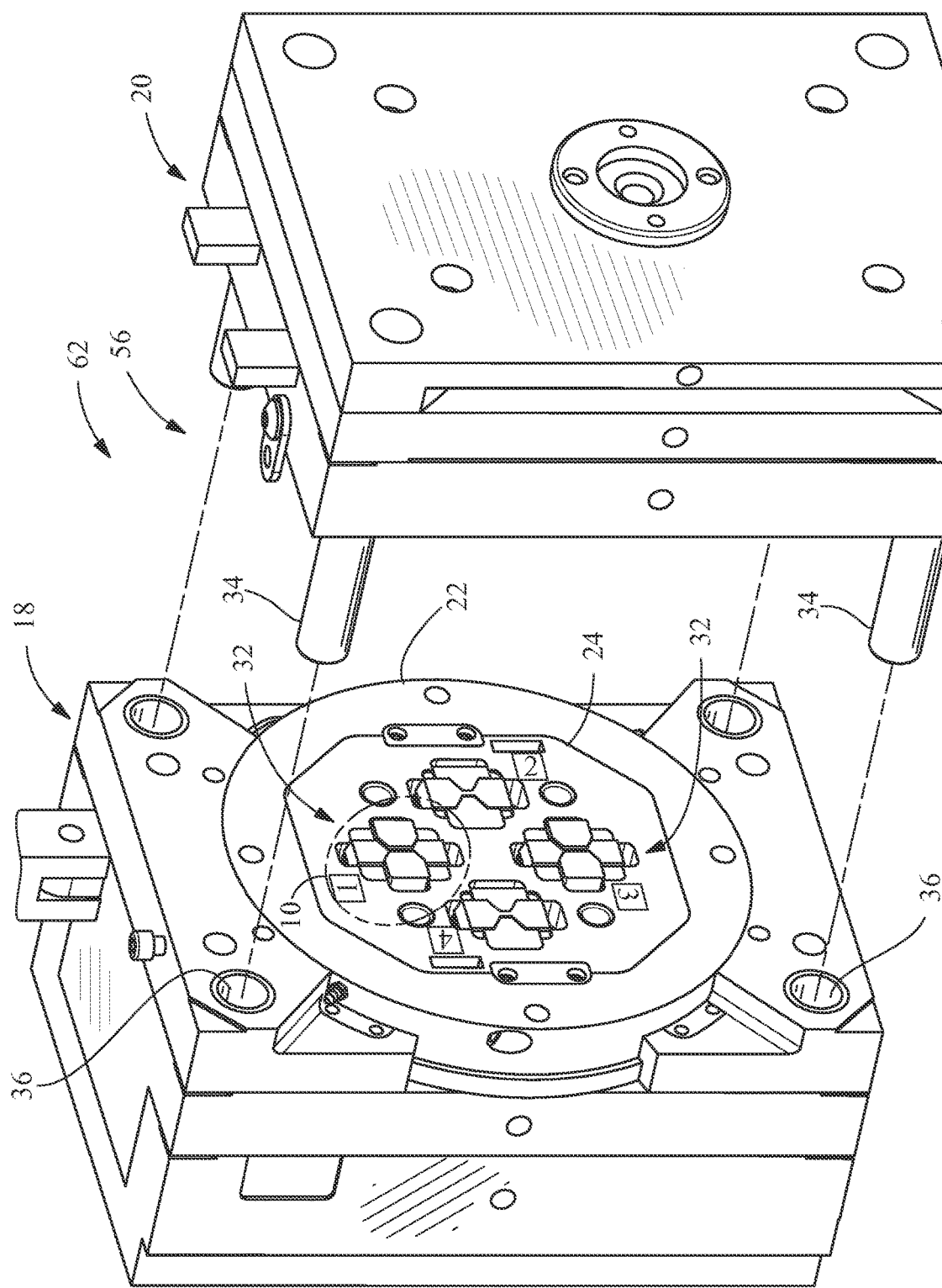
FIG. 9 is an upper perspective view of an exemplary apparatus in an open position according to the disclosure.
Figure 10:
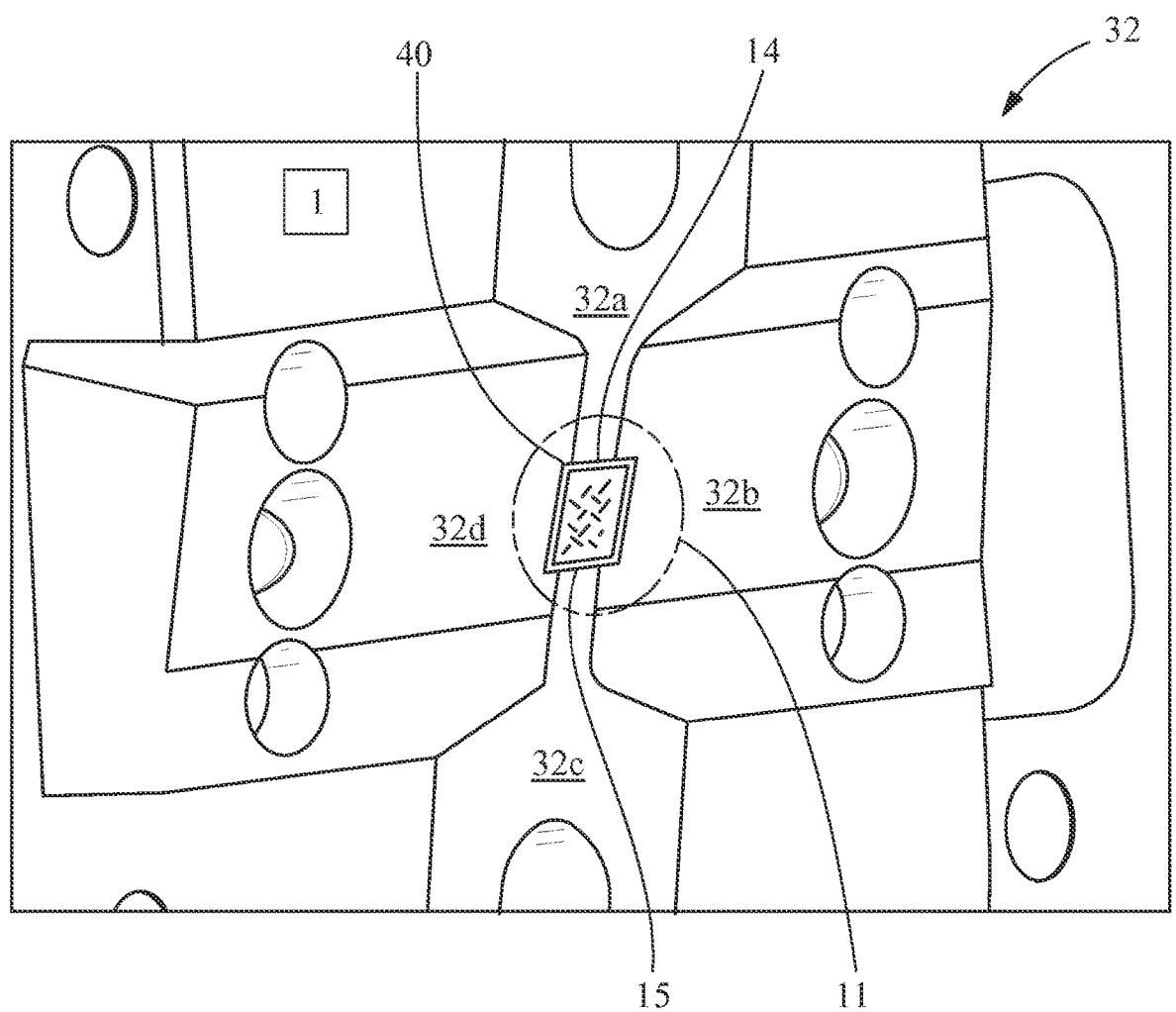
FIG. 10 is an enlarged, partial view of an exemplary initially formed article taken from region 10 of FIG. 9 according to the disclosure.

In operation, as shown in FIG. 8, with mold supports 18, 20 secured in closed position 60 (FIG. 8), mold 32 associated with boxed numeral 1 in the 12 o'clock position in first position 56 and mold 44 associated with boxed numeral 1 in the 12 o'clock position of mold support 20 (FIG. 4) receives injected material (not shown), forming injection molded article 14, as shown with mold supports 18, 20 secured in open position 62 (FIG. 9). As further shown in FIGS. 10 and 11, injection molded article 14 includes a body 15 that is secured in cavity 40 of mold segments 32a, 32b, 32c, 32d of mold segment 32. As further shown in FIG. 11, as a result of mold surface 46 of mold 44 (FIG. 6), the corresponding surface of article 14 includes a plurality of protrusions 21 extending outwardly from body 15, such as substantially circular protrusions 21a and substantially ovular protrusions 21b. However, for each of protrusions 21, the profile formed is cylindrical. That is, the cross sectional areas of protrusions 21 are either constant over the length of the protrusions, or the cross sectional areas of protrusions 21 are tapered. That is, the cross sectional areas of the protrusions decrease as the distance from body 15 increases. In one embodiment, one or more of the protrusions may contain segments of constant cross section in combination with segments having decreasing cross sectional area as the distance from the body increases (tapered profile). In one embodiment, one or more of the protrusions may extend outwardly from the body a different length from other protrusions. These cross sectional constraints of protrusions 21 are required for proper operation (clearance to permit mold removal from the rigid injection molded article) during the injection molding process as previously discussed.

In one embodiment, while mold 32 associated with the 12 o'clock position (FIG. 9) and mold 44 associated with the 12 o'clock position (FIG. 5) are forming an injection molded article 14, substantially simultaneously, mold 32 associated with the 6 o'clock position (FIG. 9) and mold 44 associated with the 6 o'clock position (FIG. 5) are also forming an injection molded article 14, as previously discussed.

Figure 12:
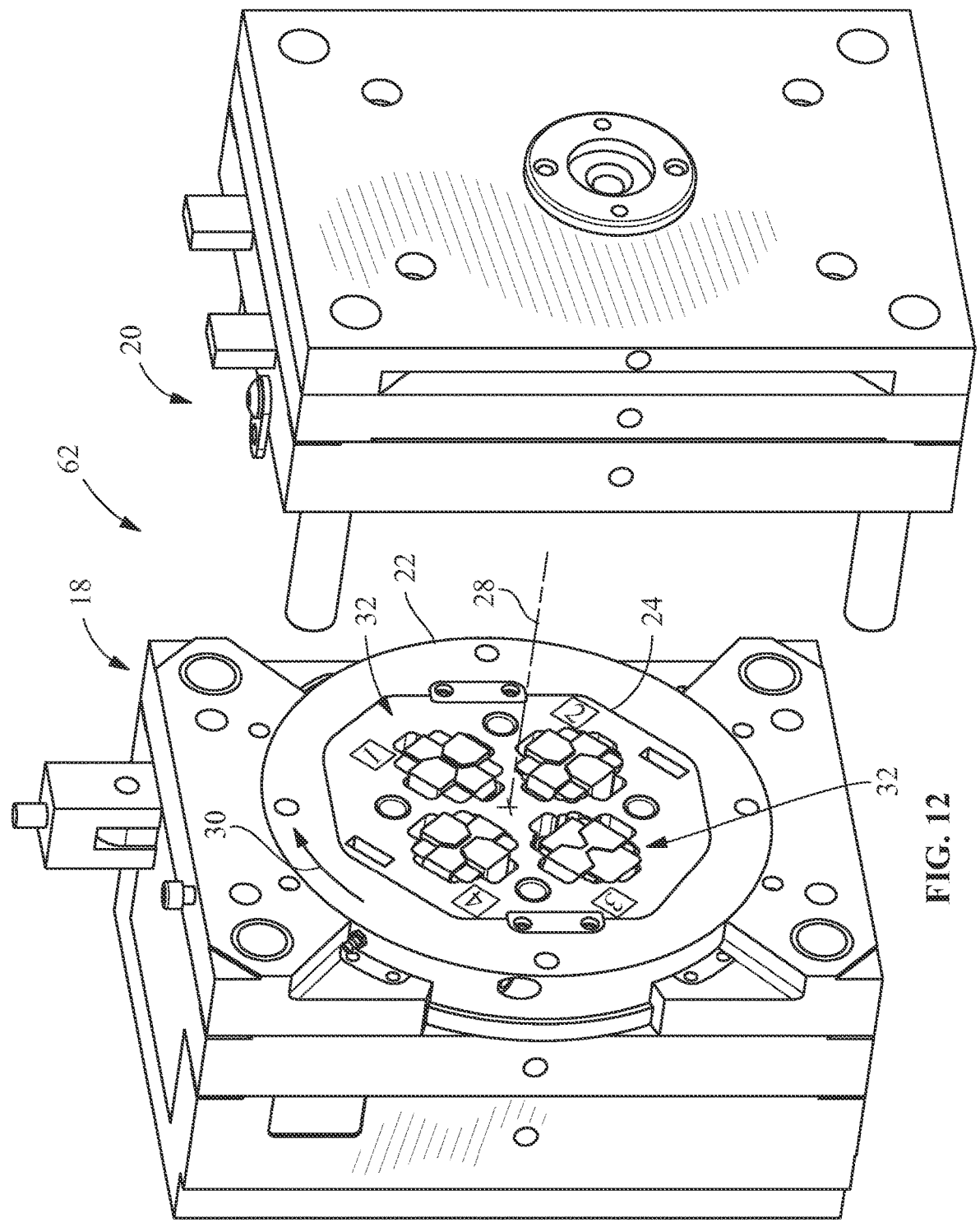
FIG. 12 is an upper perspective view of an exemplary apparatus in an open position and an exemplary mold moving between a first position and a second position according to the disclosure.

Once injection molded article 14 has been formed as discussed above, as further shown in FIGS. 12-13, mold supports 18, 20 are urged toward open position 62 and mold support portion 22 of mold support 18 is urged into rotational movement 30 about axis 28 (from first position 56 to second position 58). In second position 58, mold 32 associated with numeral 1 is rotated clockwise from the 12 o'clock position (FIG. 9) to the 3 o'clock position (FIG. 13). In one embodiment, mold 32 may be configured to rotate in a counter-clockwise direction.

Figure 15:
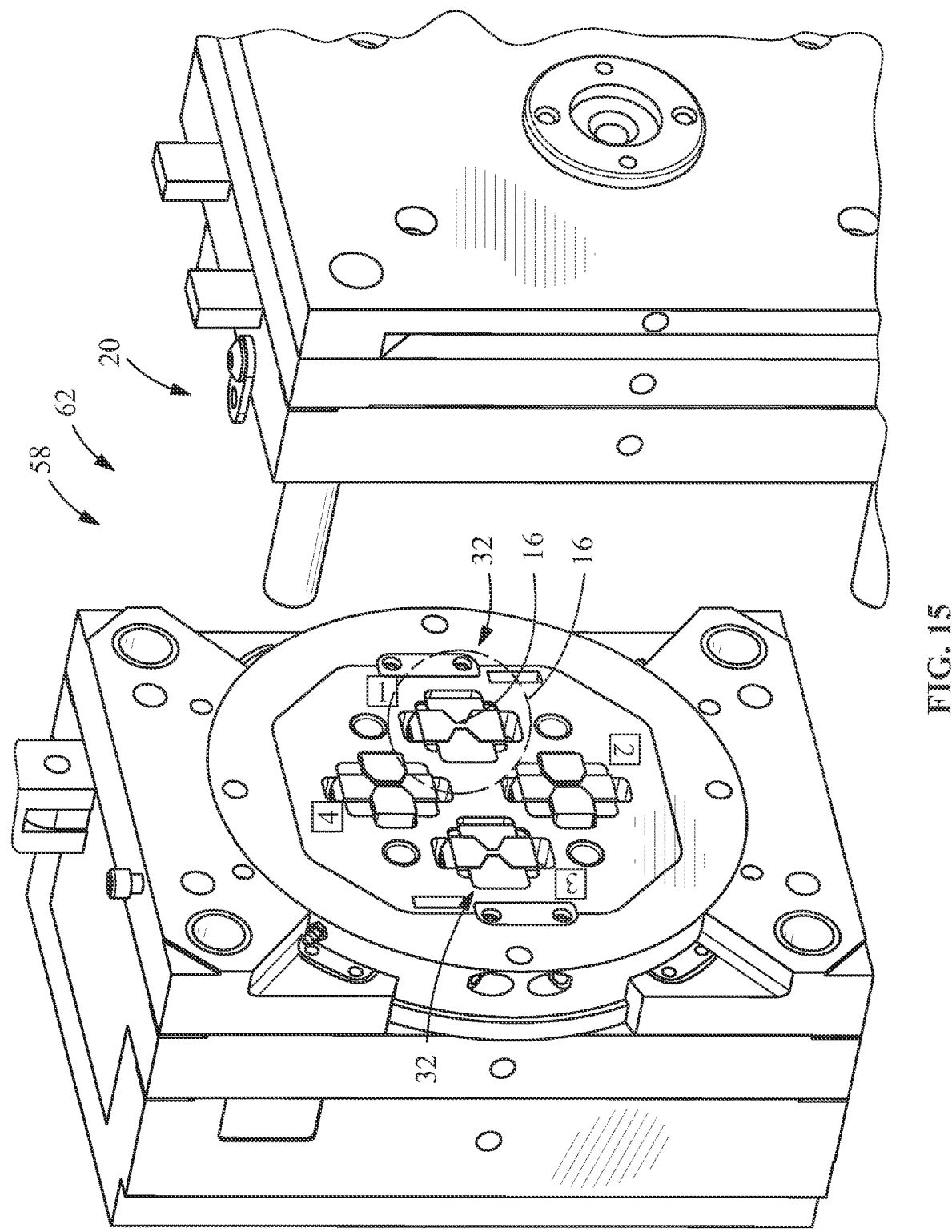
FIG. 15 is an upper perspective view of the exemplary apparatus in an open position in the exemplary mold of FIG. 13 according to the disclosure.
Figure 16:
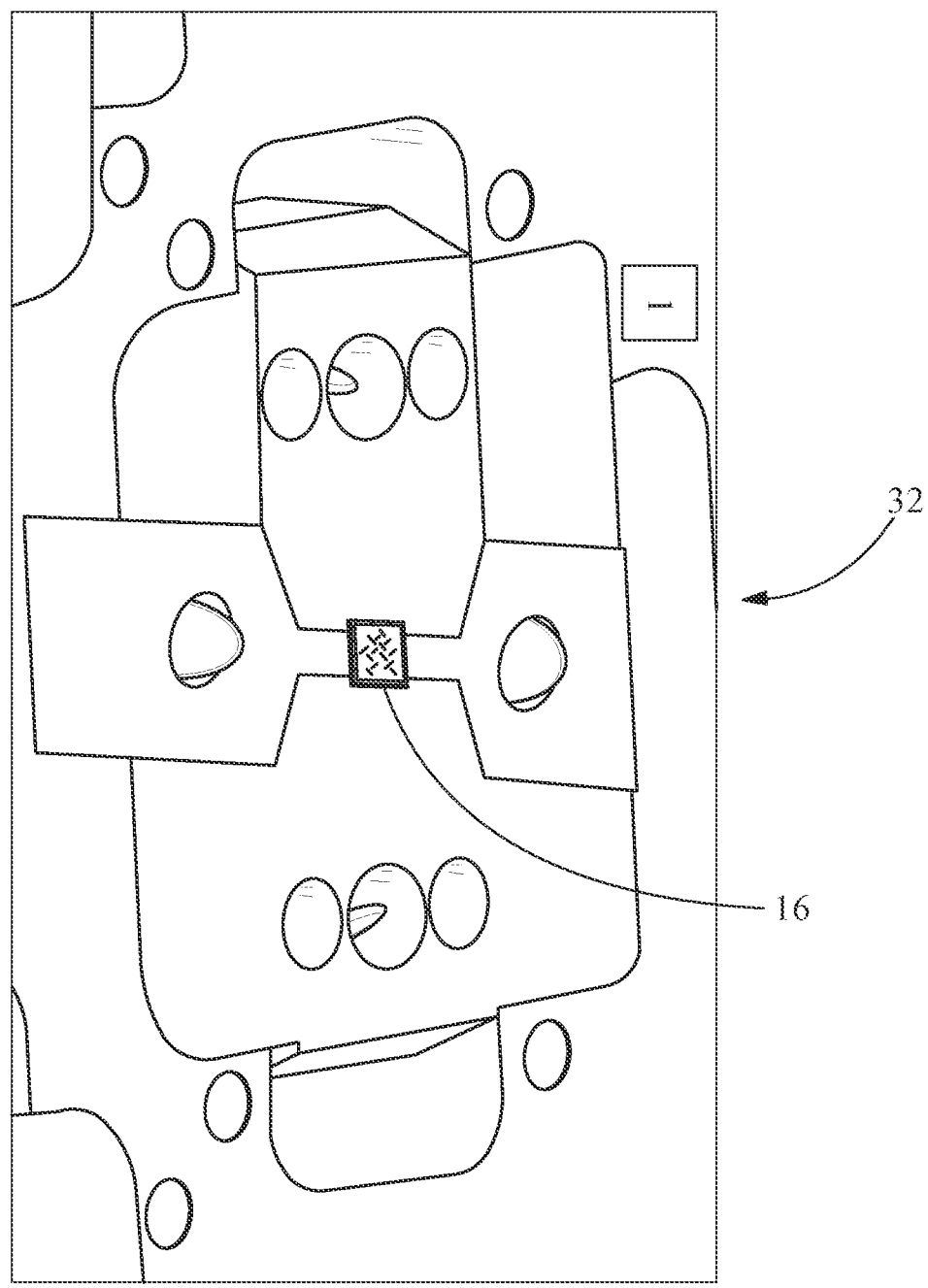
FIG. 16 is an enlarged, partial view taken from region 16 of FIG. 15 according to the disclosure.
Figure 17:
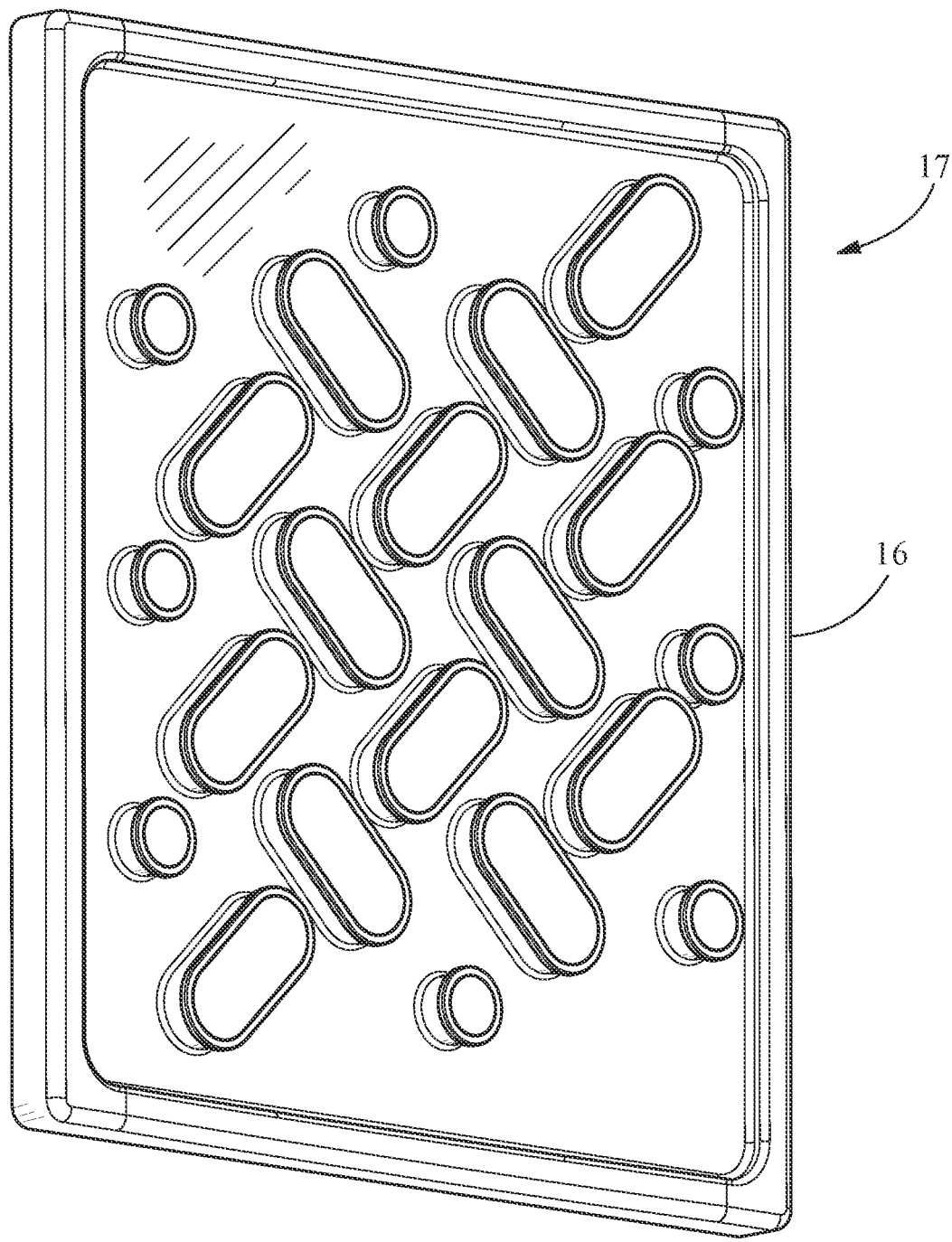
FIG. 17 is an enlarged view of an exemplary subsequently formed article of FIG. 16 according to the disclosure.

Once mold 32 associated with numeral 1 has been rotated clockwise from the 12 o'clock position (FIG. 9) to the 3 o'clock position (FIG. 13), mold supports 18, 20 are brought to closed position 60 (FIG. 14). Prior to mold supports 18, 20 being urged away from each other to open position 62 (FIGS. 15, 16), mold 32 is associated with numeral 1 and in the 3 o'clock position (with mold supports 18, 20 in closed position 60) and mold supports 18, 20 are brought together with die surface 54 of die 48 associated with numeral 2 and in the 9 o'clock position (FIGS. 4, 5, 7)). As a result, die surface 54 of die 48 creates subsequently formed protrusions 17 of subsequently formed article 16 (formerly injection molded article 14).

In one embodiment, while mold 32 associated with the 3 o'clock position (FIG. 15) and die 48 associated with the 9 o'clock position (FIG. 5) are creating a subsequently formed article 16, substantially simultaneously, mold 32 associated with the 9 o'clock position (FIG. 9) and die 48 associated with the 3 o'clock position (FIG. 5) are also creating a subsequently formed article 16, as previously discussed.

In one embodiment, while molds 32 are brought together with corresponding molds 44 to form injection molded articles 14, substantially simultaneously, the remaining molds 32 are brought together with corresponding dies 48 to create subsequently formed articles 16. In other words, apparatus 12 can operate continuously to form or create subsequently formed articles 16 (from previously formed injection molded articles 14) while substantially simultaneously forming additional articles 14. That is, with each 90 degree rotation of mold support portion 22 of mold support 18 relative to mold support 20, one pair of injection molded articles 14 are created, and one pair of subsequently formed articles 16 are formed or created continuously by the apparatus of the present disclosure.

Figure 11:
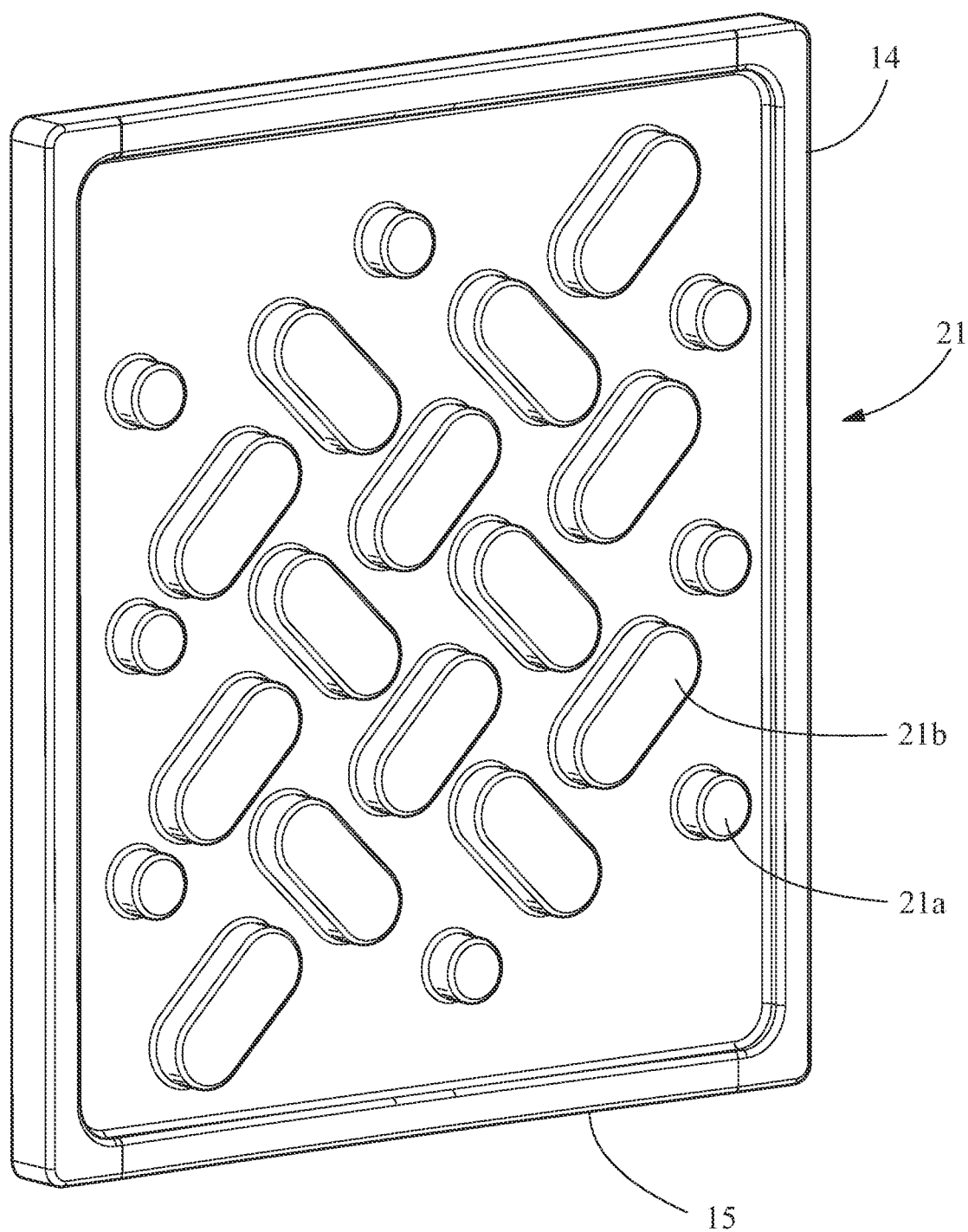
FIG. 11 is an enlarged, partial view of the exemplary initially formed article taken from region 11 of FIG. 10 according to the disclosure.
Figure 18:
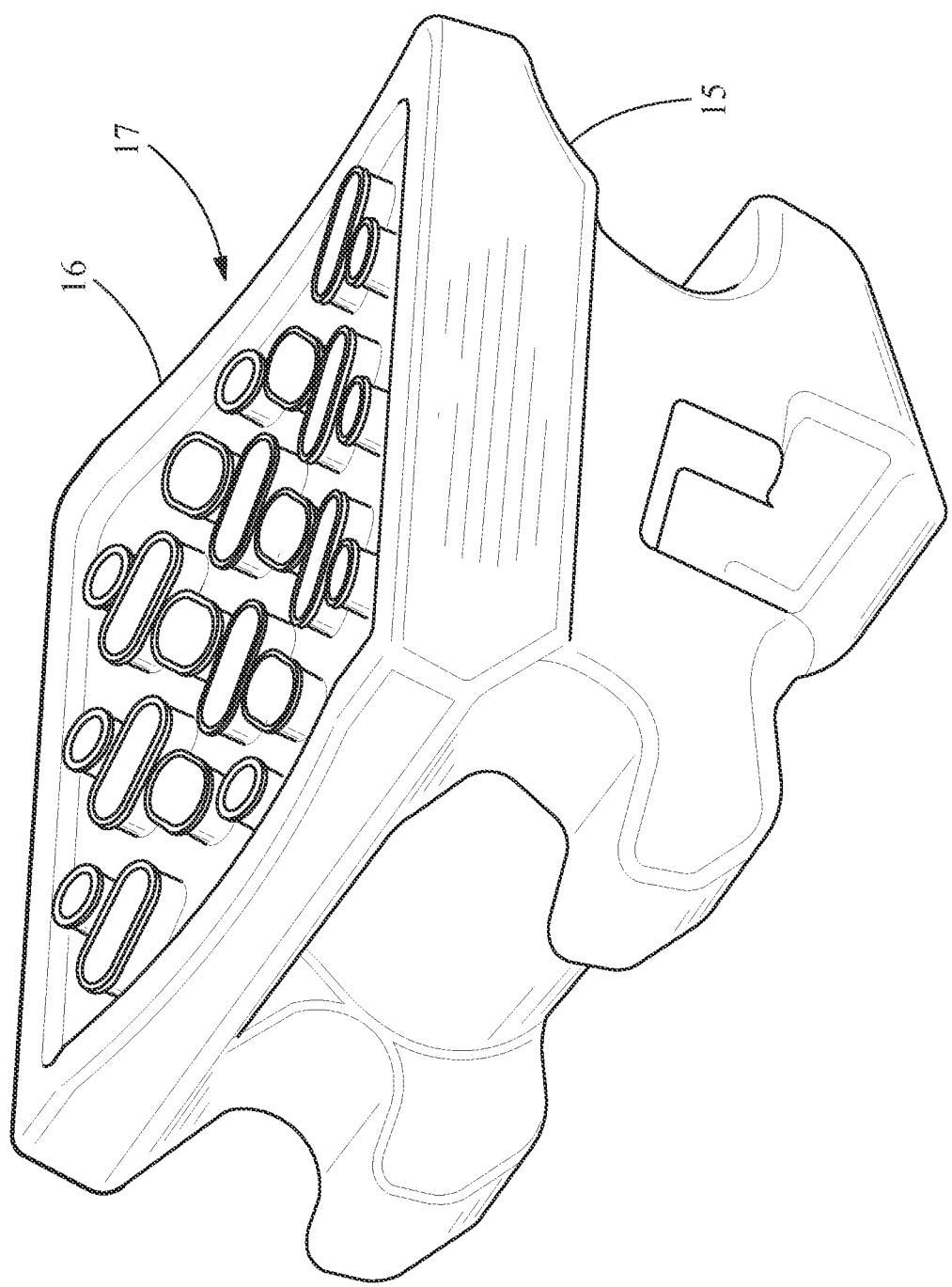
FIG. 18 is an upper perspective view of an exemplary (subsequently formed) orthodontic bracket of FIG. 16 according to the disclosure.
Figure 19:
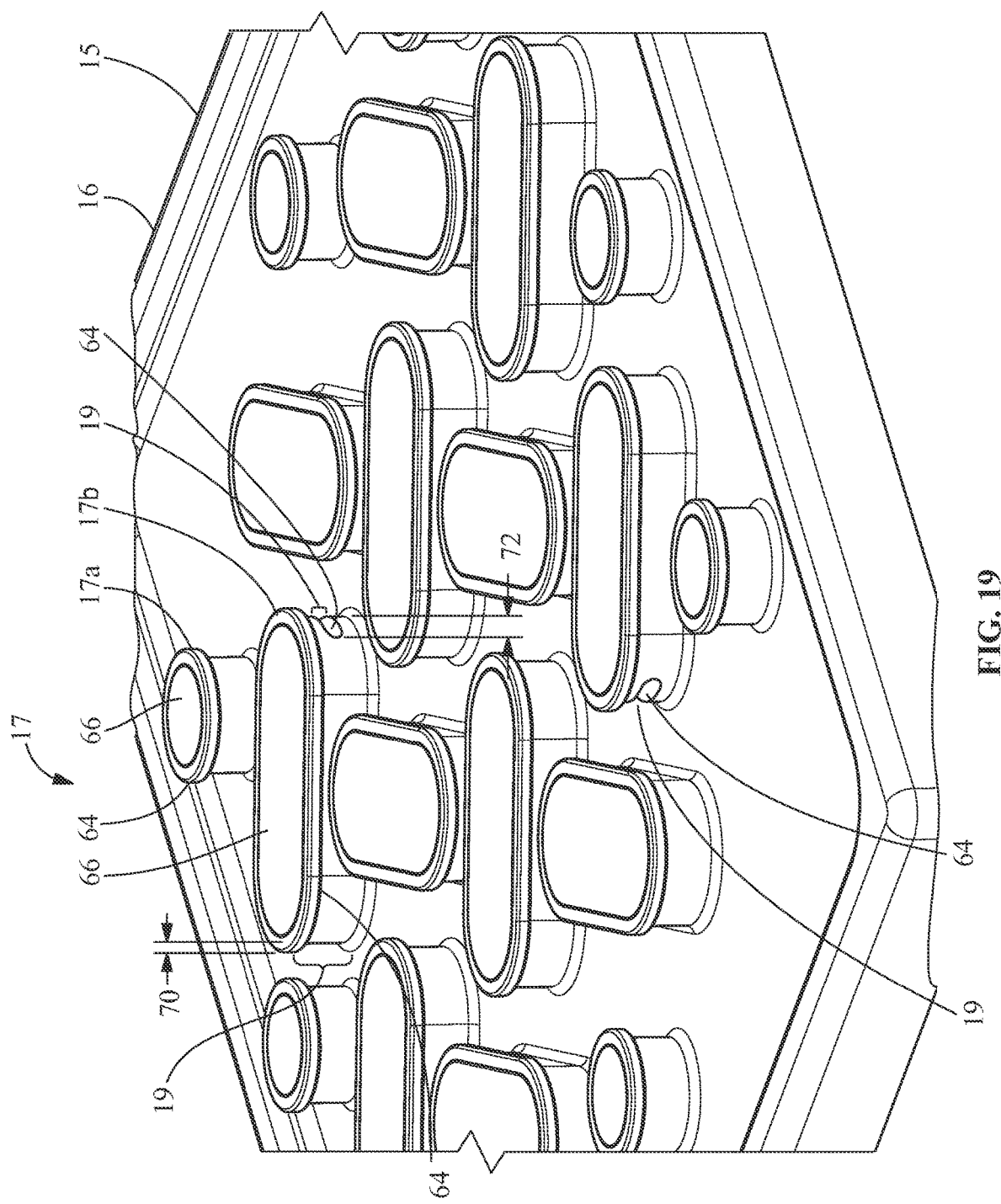
FIG. 19 is an enlarged, partial view of the orthodontic bracket of FIG. 18 according to the disclosure.

As further shown in FIGS. 18 and 19, in which subsequently formed article 16 has been ejected from the injection molder, the differences between injection molded articles 14 and subsequently formed articles 16 are readily apparent and significant. That is, as shown in FIG. 11, injection molded article 14 includes protrusions 21, including protrusions 21a, 21b each having cylindrical profiles (i.e., defining constant cross sectional areas over the length of the protrusions, or a decrease in cross sectional areas over the length of the protrusions as the distance from body 15 increases) for reasons as previously discussed. In contrast, as further shown in FIGS. 18 and 19, subsequently formed article 16 includes subsequently formed protrusions 17, including subsequently formed protrusions 17a, 17b, having an undercut 19 formed in an altered cross sectional region 64 or between altered cross sectional region 64 of protrusion 17, such as in close proximity to an end 66, and body 15, such as when the altered cross sectional region has a cross sectional area greater than the cross sectional area of the protrusion (in which case undercut 19 is formed between altered cross sectional region 64 and body 15). In one embodiment, altered cross sectional region 64 is at least a localized region of enlarged cross sectional area relative to the cross sectional area of the protrusion. In one embodiment, altered cross sectional region 64 of protrusion 17 is not in close proximity to end 66 of body 15. In one embodiment, such as shown in FIG. 19, altered cross sectional region 64 is at least a localized region of reduced cross sectional area relative to the cross sectional area of the protrusion forming undercut 19, so long as the localized region is not at or in such close proximity to end 66 so as not to provide a basis for improved adhesion between an adhesive and the protrusion. The formation of an undercut 19 provides a basis for improved adhesion of a surface including the subsequently formed protrusions 17, as hardened adhesive material may form an interference fit defined by the difference in cross sectional area between the undercut and a corresponding altered cross sectional region 64, such as an undercut 70 when the altered cross sectional region 64 has a greater cross sectional area than the undercut. However, when the altered cross sectional region 64 has a reduced cross sectional area relative to the cross sectional area of the protrusion (and not proximate to end 66), the undercut 19 is formed in or is coincident with the altered cross sectional region 64 and having an undercut depth 72.

In one embodiment, protrusions 17 can define a closed geometry, such as a substantially circular or substantially ovular profile, while in another embodiment, protrusions 17 can define an open geometry, such as a profile similar to a crescent moon, or any suitable shape. The protrusions may be positioned in any suitable arrangement relative to one another, singly or collectively.

It is to be understood that the profile of the die surface of the die is not limited to closely resemble the protrusion profile formed in the injection molded article 14, so long as the profiles of the subsequently formed protrusions 17 have a desired undercut profile. That is, in one embodiment, the position of altered cross sectional regions can be formed in a position other than the end or in close proximity to the end of the subsequently formed protrusions, if desired. In another embodiment, the position of the die surface is movable relative to the mold support. That is, the die surface may be positioned at a desired spacing from the protrusion surface of the injection molded article when the corresponding mold supports are brought together, which spacing includes positioning the die surface such that a selective amount of interference or abutment occurs between ends of one or more protrusions of the injection molded article 14 and the die surface, such that the subsequently formed protrusion(s) is selectively controllable. In one embodiment, a non abutting spacing remains between the die surface and the corresponding surface of the injection molded article 14 when the mold supports are brought together.

In addition, the die can be brought into a predetermined range of at least one position relative to the protrusion(s) of the injection molded article for a corresponding predetermined range of time for subjecting at least a portion of the protrusion(s) to one or more of a predetermined temperature range and a predetermined pressure range for forming the undercut. That is, the temperature of the die (of course, including the die surface) can be selectively controlled as a function of distance or proximity of the die from the protrusion(s) of the injection molded article in combination with a predetermined rate of time. In addition, the temperature of portions of the die can be selectably controlled over a predetermined range of temperatures as well as a predetermined rate of time. In other words, the temperature of the die (and even portions of the die) can be selectively controlled in combination with the speed of travel of the die (toward and/or away from protrusion(s) of the injection molded article; such speeds not limited to being the same in either direction) and/or the amount of proximity or spacing from the protrusion(s), including a range of abutment between the die and the protrusion(s) of the injection molded article. Stated another way, the die can be selectively controlled over a broad range of temperatures, such temperatures also being selectively controllable relative to the speed and/or distance from the protrusion(s), including interference or abutment, as well as selective control of time. In one embodiment, the die may be configured to remain in a non-moving position (also referred to as dwell time) for at least a portion of the time that the mold supports are brought together. In one embodiment, the die selectively controls a surface feature of at least a portion of the protrusion(s). For example, if the die surface contacts the protrusion(s), the surface roughness of the die may be transferred at least to the extent of the amount of contact of the protrusion(s) and the die surface. As a result of the extent of control of the die relative to the protrusion(s) of the injection molded article, at least the position and magnitude of undercut may be selectively controlled for the protrusion(s), and the amount of subsequent forming of the protrusion(s) may be altered during production.

It is also to be understood that materials which may be used in the apparatus can be liquid or powdered forms of ceramic, metal, plastic material or a combination thereof, depending upon the application.

It is also to be understood that while the article disclosed is an orthodontic bracket, the apparatus of the present disclosure may also be used for any number of other injection molded articles in which a secondary forming operation subsequent to production of the injection molded article can provide beneficial effects, not being limited to forming undercuts, such as surface features or other beneficial properties derivable from such secondary forming operations.

Figure 20:
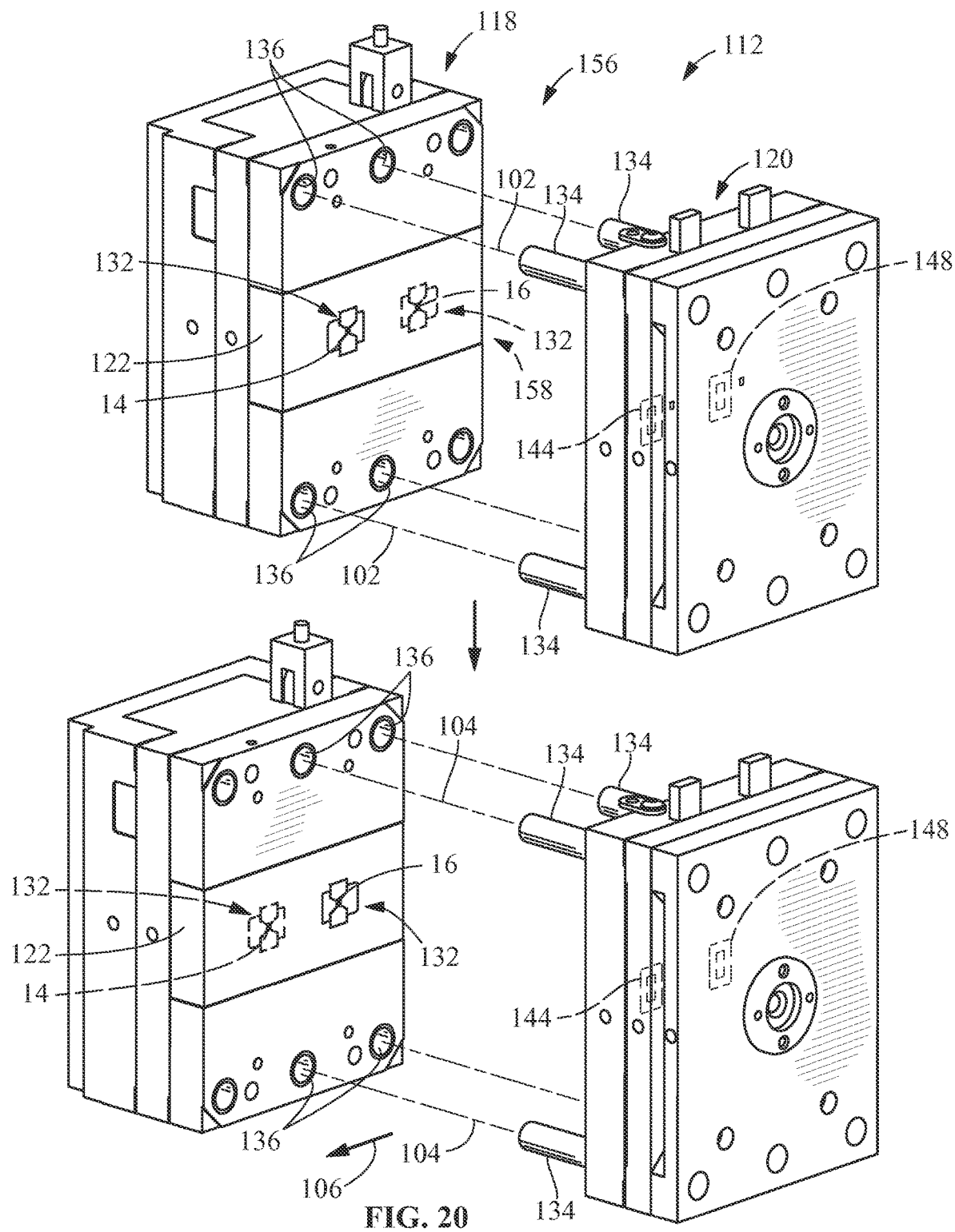
FIG. 20 is an upper perspective view of an exemplary apparatus in an open position and an exemplary mold in a first position according to the disclosure.
Figure 21:
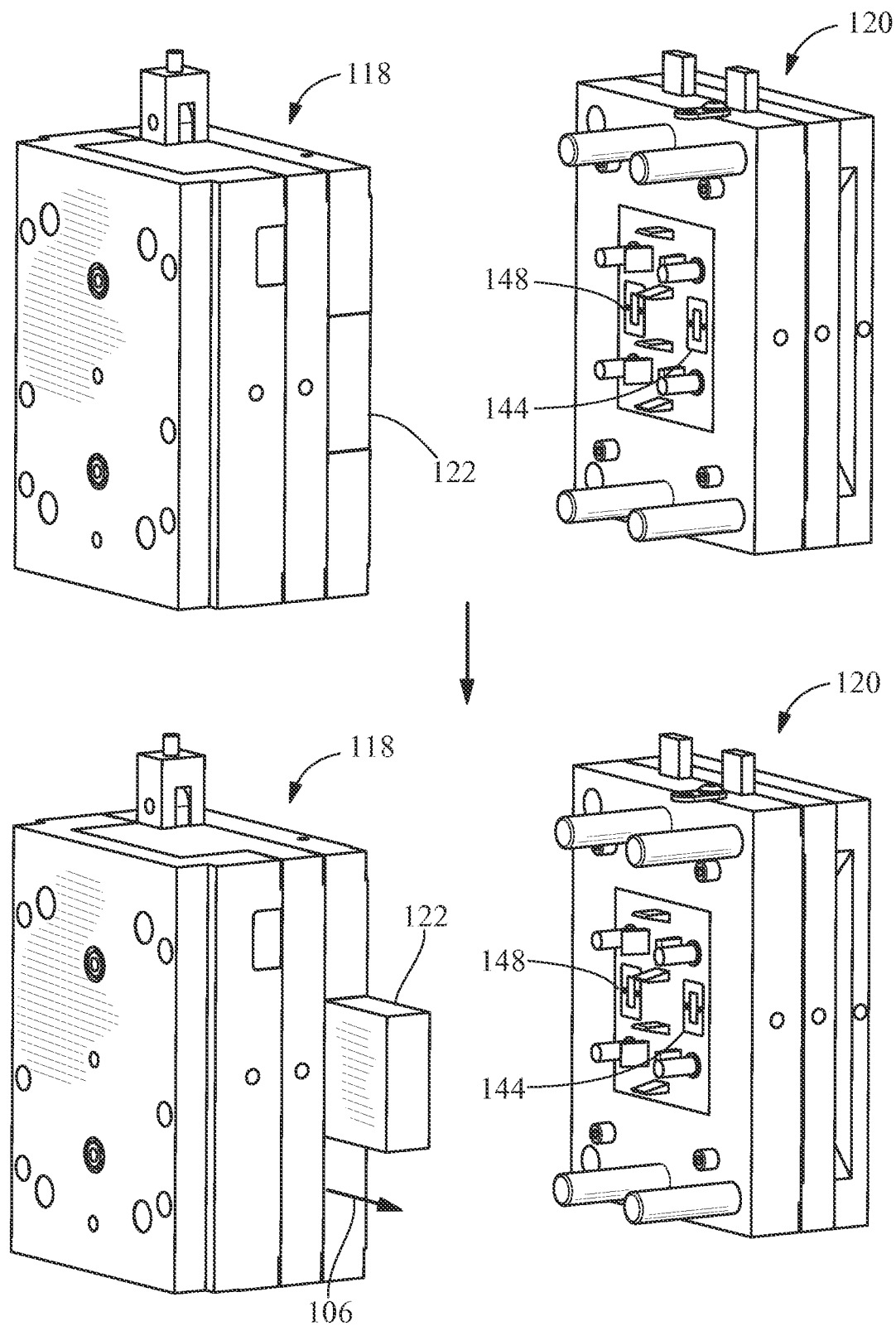
FIG. 21 is a reverse upper perspective view, relative to FIG. 20, of the exemplary apparatus of FIG. 20 according to the disclosure.

As shown in FIGS. 20 and 21, in a manner similar to that previously discussed, apparatus 112 includes a mold support 118 having a mold 132 and a mold support 120 having a mold 144 and the die 148, with mold support 118 being movable between a first position 156 and a second position 158 relative to mold support 120. As shown in FIG. 20, mold support 122 can be urged into directional movement 106, which movement being linear, or curvilinear, if desired. In a manner similar to that previously discussed, in response to movement of mold support 122 and/or of line of engagement 102, 104 between mold supports 118, 120, mold 132 and mold 144 can be aligned and brought together for forming an injection molded article 14, or mold 132 and die 148 can be aligned and brought together for subsequently forming article 16 (formerly injection molded article 14).

Figure 22:
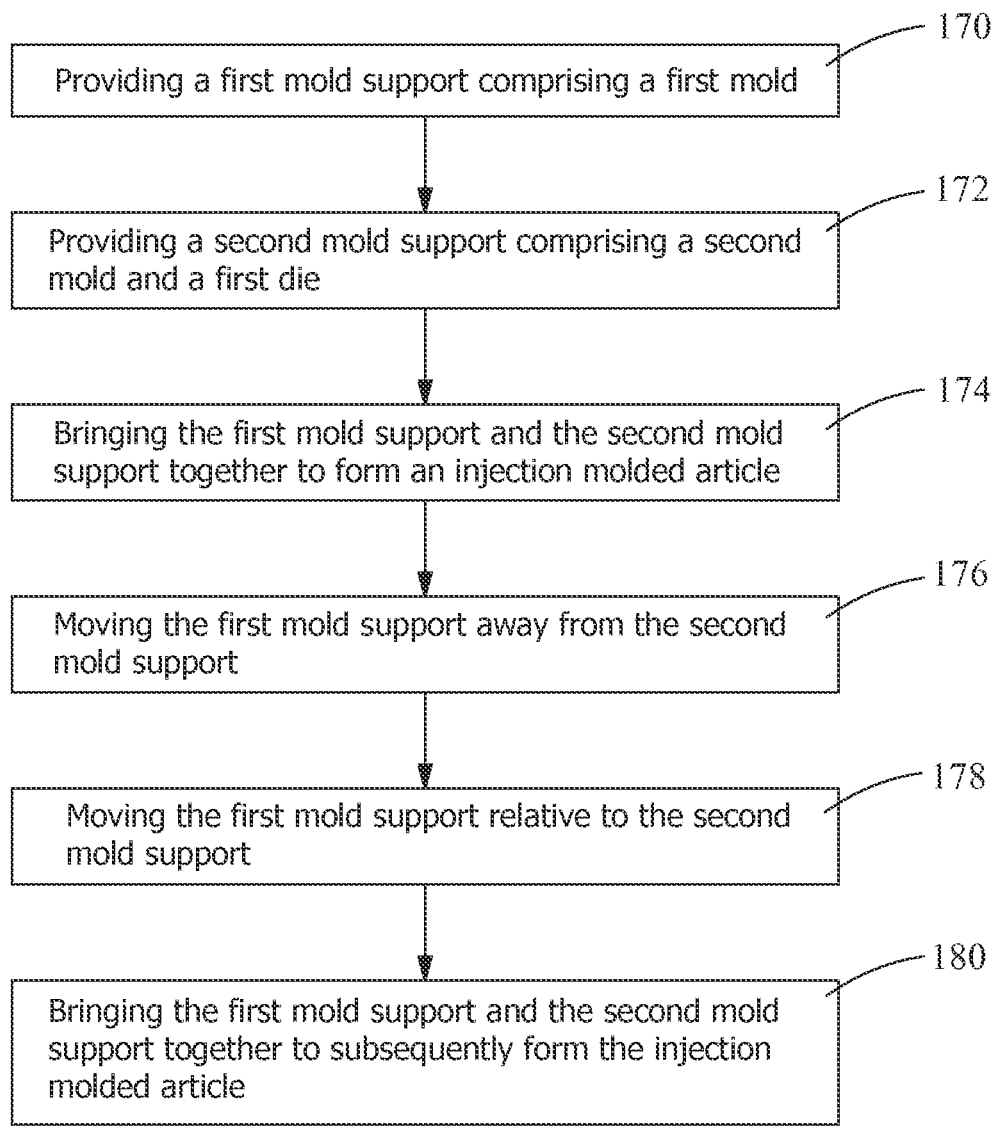
FIG. 22 is a process diagram corresponding with the operation of an exemplary apparatus according to the disclosure.

As shown in FIG. 22, a method of producing injection molded articles includes providing a first mold support 18 comprising a first mold 32 in step 170. In addition, step 172 includes providing a second mold support 20 comprising a second mold 44 and a first die 48. Once the components of steps 170 and 172 have been completed, step 174 includes bringing the first mold support 18 and the second mold support 20 together to form an injection molded article 14 therebetween, the article 14 having a body 15 having at least one protrusion 21 facing the second mold 44. After injection molded article 14 has been formed, the first mold support 18 is moved away from the second mold support 20 in step 176. Once the first mold support 18 has been moved away from the second mold support 20, the first mold support 18 is moved relative to the second mold support 20 in step 178. Once the first mold support 18 is moved relative to the second mold support 20, in step 180, the first mold support 18 and the second mold support 20 are brought together to subsequently form at least a portion of the subsequently formed protrusion 17 (previously the protrusion 21 of injection molded article 14), the first die 48 selectively subsequently forming at least a portion of the subsequently formed protrusion 17, forming an undercut 19 between an end 66 of the subsequently formed protrusion 21 and the body 15.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material including dopants to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus usable with an injection molder for producing articles, comprising:

a first mold support comprising a first mold;
a second mold support comprising a second mold and a first die;
the first mold support movable relative to the second mold support between a first position and a second position;
wherein in the first position, the first mold and the second mold being brought together to form an injection molded article comprising a body having at least one protrusion extending outwardly from the body and facing the second mold;
wherein in the second position, the first mold and the first die being brought together to form a subsequently formed article, the first die selectively subsequently forming a first altered cross sectional region in at least a first portion of the protrusion, forming a first undercut in the first altered cross sectional region or between the first altered cross sectional region of the protrusion and the body, the first undercut proximate to an end of the protrusion, the first die adapted to form a second altered cross sectional region in at least a second portion of the protrusion, forming a second undercut, the second undercut non-proximate to the end of the protrusion;
wherein the article is an orthodontic bracket.

2. The apparatus of claim 1, wherein the first mold support is rotatably movable about an axis relative to the second mold support.

3. The apparatus of claim 1, wherein the first mold support is movable along a line relative to the second mold support.

4. The apparatus of claim 1, wherein at least the first mold support comprises a plurality of first molds and the second mold support comprises at least one second mold and at least one first die, the apparatus operable such that once at least one first mold and at least one second mold have been brought together to form the article (the first position), when the at least one first mold and the at least one first die are then brought together to form the subsequently formed article (the second position), another of the at least one first mold and another of the at least one second mold are substantially simultaneously brought together to form another article (a third position).

5. The apparatus of claim 4, wherein the corresponding first molds, second mold(s) and first die(s) of the apparatus operate continuously to form subsequently formed articles while substantially simultaneously forming additional articles.

6. The apparatus of claim 1, wherein the protrusion comprises an open geometry.

7. The apparatus of claim 1, wherein the protrusion comprises a closed geometry.

8. The apparatus of claim 1, wherein the first die is brought into a predetermined range of at least one position relative to the protrusion for a corresponding predetermined range of time for subjecting the at least a first portion and the at least a second portion of the protrusion to one or more of a predetermined temperature range and a predetermined pressure range for forming the first undercut and the second undercut.

9. The apparatus of claim 8, wherein the temperature of portions of the first die is selectively controllable for the predetermined range of at least one position and the corresponding predetermined range of time.

10. The apparatus of claim 1, wherein the article is formed from a ceramic, metal, plastic material or a combination thereof.

11. The apparatus of claim 8, wherein the first die selectively controls a surface feature of at least one of the at least a first portion and the at least a second portion of the protrusion.

12. An apparatus usable with an injection molder for producing articles, comprising:
a first mold support comprising at least two first molds;
a second mold support comprising at least two second molds and at least two first dies;
the first mold support rotatably movable relative to the second mold support between a first position and a second position;
wherein in the first position, each of the corresponding first molds and second molds being brought together to form an injection molded article comprising a body having at least one protrusion extending outwardly from the body and facing the second mold;
wherein in the second position, each of the corresponding first molds and first dies being brought together to form a subsequently formed article, each first die selectively subsequently forming a first altered cross sectional region in at least a first portion of the protrusion, forming a first undercut in the first altered cross sectional region or between the first altered cross sectional region of the protrusion and the body, the first undercut proximate to an end of the protrusion, the first die adapted to form a second altered cross sectional region in at least a second portion of the protrusion, forming a second undercut, the second undercut non-proximate to the end of the protrusion;
wherein the article is an orthodontic bracket.

13. The apparatus of claim 12, wherein the corresponding first molds, second molds and first dies of the apparatus operate continuously to form subsequently formed articles while substantially simultaneously forming additional articles.

14. The apparatus of claim 12, wherein each first die is brought into a predetermined range of at least one position relative to the corresponding protrusion for a corresponding predetermined range of time for subjecting the at least a first portion and the at least a second portion of the protrusion to one or more of a predetermined temperature range and a predetermined pressure range for forming the undercut.

15. The apparatus of claim 14, wherein the temperature of portions of the first die is selectively controllable for the predetermined range of at least one position and the corresponding predetermined range of time.

16. The apparatus of claim 12, wherein the article is formed from a ceramic, a metal, a plastic or a combination thereof.

17. The apparatus of claim 14, wherein the first die selectively controls a surface feature of the at least a first portion and the at least a second portion of the protrusion.

18. A method of producing injection molded articles, comprising:
providing a first mold support comprising a first mold, a second mold support comprising a second mold and a first die,
bringing the first mold support and the second mold support together in a first position, the first mold and the second mold being brought together to form an injection molded article therebetween, wherein the article is an orthodontic bracket, the article having at least one protrusion facing the second mold;
moving the first mold support away from the second mold support;

moving the first mold support relative to the second mold support;

bringing the first mold support and the second mold support together in a second position, the first mold and the first die being brought together to form a subsequently formed article, the first die selectively subsequently forming a first altered cross sectional region in at least a first portion of the protrusion, forming a first undercut in the first altered cross sectional region or between the first altered cross sectional region of the protrusion and the body, the first undercut proximate to an end of the protrusion, the first die adapted to form a second altered cross sectional region in at least a second portion of the protrusion, forming a second undercut, the second undercut non-proximate to the end of the protrusion.

19. The method of claim 18, wherein providing a first mold support comprises a plurality of first molds, and subsequent to moving the first mold support relative to the second mold support, bringing the first mold support and the second mold support together such that once at least one first mold and at least one second mold have been brought together to form the article, when the at least one first mold and the at least one first die are then brought together to form the subsequently formed article, another first of the at least one mold and another of the at least one second mold are substantially simultaneously brought together to form another article.

* * * * *